US010369166B2

(12) United States Patent
Vecht-Lifshitz

(10) Patent No.: US 10,369,166 B2
(45) Date of Patent: Aug. 6, 2019

(54) PHARMACEUTICAL COMPOSITIONS FOR TREATING EBOLA VIRUS DISEASE

(71) Applicant: Susan Eve Vecht-Lifshitz, Jerusalem (IL)

(72) Inventor: Susan Eve Vecht-Lifshitz, Jerusalem (IL)

( * ) Notice: Subject to any disclaimer, the term of this patent is extended or adjusted under 35 U.S.C. 154(b) by 0 days.

(21) Appl. No.: 15/514,520

(22) PCT Filed: Sep. 20, 2015

(86) PCT No.: PCT/IL2015/000043

§ 371 (c)(1),
(2) Date: Mar. 26, 2017

(87) PCT Pub. No.: WO2016/051396

PCT Pub. Date: Apr. 7, 2016

(65) Prior Publication Data

US 2017/0232032 A1 Aug. 17, 2017

Related U.S. Application Data

(60) Provisional application No. 62/057,268, filed on Sep. 30, 2014, provisional application No. 62/079,136, filed on Nov. 13, 2014.

(51) Int. Cl.

| | |
|---|---|
| ***A61K 31/706*** | (2006.01) |
| ***A61P 31/14*** | (2006.01) |
| ***A61K 31/7076*** | (2006.01) |
| ***A61K 45/06*** | (2006.01) |
| ***A61K 31/12*** | (2006.01) |
| ***A61K 31/375*** | (2006.01) |
| ***A61K 31/437*** | (2006.01) |
| ***A61K 31/05*** | (2006.01) |
| ***A61K 31/19*** | (2006.01) |
| ***A61K 31/198*** | (2006.01) |
| ***A61K 31/352*** | (2006.01) |
| ***A61K 31/353*** | (2006.01) |
| ***A61K 31/365*** | (2006.01) |
| ***A61K 31/4745*** | (2006.01) |
| ***A61K 31/7048*** | (2006.01) |
| ***A61K 33/00*** | (2006.01) |
| ***A61K 31/4375*** | (2006.01) |
| ***A61K 31/569*** | (2006.01) |
| ***A61K 33/24*** | (2019.01) |
| ***A61K 38/06*** | (2006.01) |
| ***A61K 31/205*** | (2006.01) |
| ***A61K 36/258*** | (2006.01) |

(52) U.S. Cl.

CPC .......... *A61K 31/7076* (2013.01); *A61K 31/05* (2013.01); *A61K 31/12* (2013.01); *A61K 31/19* (2013.01); *A61K 31/198* (2013.01); *A61K 31/205* (2013.01); *A61K 31/352* (2013.01); *A61K 31/353* (2013.01); *A61K 31/365* (2013.01); *A61K 31/375* (2013.01); *A61K 31/437* (2013.01); *A61K 31/4375* (2013.01); *A61K 31/4745* (2013.01); *A61K 31/569* (2013.01); *A61K 31/706* (2013.01); *A61K 31/7048* (2013.01); *A61K 33/00* (2013.01); *A61K 33/24* (2013.01); *A61K 36/258* (2013.01); *A61K 38/06* (2013.01); *A61K 45/06* (2013.01); *A61P 31/14* (2018.01)

(58) Field of Classification Search

None

See application file for complete search history.

(56) References Cited

U.S. PATENT DOCUMENTS

| | | | | |
|---|---|---|---|---|
| 6,911,435 B1 * | 6/2005 | Cohn | A61K 31/70 | 514/46 |
| 8,580,762 B2 * | 11/2013 | Olhava | C07D 487/04 | 514/46 |
| 2006/0020046 A1 * | 1/2006 | Goralczyk | A61K 31/01 | 514/763 |
| 2008/0287541 A1 * | 11/2008 | Hoffman | A61K 45/06 | 514/562 |

FOREIGN PATENT DOCUMENTS

| | | | | |
|---|---|---|---|---|
| CN | 103720690 | * | 4/2014 | A61P 35/02 |
| WO | WO2014/039839 | * | 3/2014 | A61K 31/52 |
| WO | WO2014/077784 | * | 5/2014 | A61K 38/21 |
| WO | 2014100662 A1 | | 6/2014 | |
| WO | 2014152562 A1 | | 9/2014 | |

OTHER PUBLICATIONS

Huggins et al., "Antiviral Drug Therapy of Filovirus Infections: S-Adenosylhonnocysteine Hydrolase Inhibitors Inhibit Ebola Virus In Vitro and in a Lethal Mouse Model" Journal of Infectious Diseases (1999) vol. 179 suppl 1, pp. S240-S247 (Year: 1999).*

Kim et al., "Induction of apoptosis in human leukemia cells by 3-deazaadenosine is mediated by caspase-3-like activity" Experimental and Molecular Medicine (2000) vol. 32 No. 4 pp. 197-203 (Year: 2000).*

Momparler et al., "Synergistic antileukemic action of a combination of inhibitors of DNA methylation and histone methylation" Leukemia Research (2012) vol. 36 pp. 1049-1054 (Year: 2012).*

English abstract and machine translation of CN103720690, downloaded from worldwide.espacenet.com (Year: 2014).*

(Continued)

*Primary Examiner* — Eric Olsen

(74) *Attorney, Agent, or Firm* — Eva Taksel

(57) ABSTRACT

The present invention provides compounds and pharmaceutical compositions adapted to reduce a load of an RNA virus by at least 50%, the virus causing a pathogenic disease in a mammalian subject, the compound adapted to inhibit the formation of S-adenosyl methionine (SAM) in the virus, the compound being a DOTIL inhibitor, wherein the compound has a molecular weight of less than 1000, and a therapeutic index (TI=LD.sub.50:ED.sub.50) greater than 30 in the mammalian subject.

9 Claims, No Drawings

(56) References Cited

OTHER PUBLICATIONS

Chemical Abstracts Registry entry for CAS#6736-58-9 (3-deazaadenosine), downloaded from STN file Registry (Year: 2018).*

Med Chem Express database entry for EPZ-5676 (CAS# 1380288-87-8) downloaded from https://www.medchemexpress.com/ (Year: 2018).*

Marty et al., "Viral Hemorrhagic Fevers" Clinics in Laboratory Medicine vol. 26 pp. 345-386 (Year: 2006).*

Supplementary European Search Report of the EPO, dated Jan. 23, 2018.

* cited by examiner

PHARMACEUTICAL COMPOSITIONS FOR TREATING EBOLA VIRUS DISEASE

FIELD OF THE INVENTION

The present invention relates generally, to methods for treating a disease and more specifically to statistical-based methods for treating a disease.

BACKGROUND OF THE INVENTION

There are several viral disease which have no or limited treatment options. Ebola virus, Marburg virus, Dengue virus are viruses with poor primate and/or human survival statistics. Many other viruses may be fatal, particularly in young children, the elderly or immunocompromised patients.

To date, most research groups are looking for a "one drug treatment" or "perfect fit immunological solution" such as a vaccine or monoclonal antibody.

RNA virus families include Arenaviridae, Filoviridae, Bunyaviridae, Flaviviridae, and Rhabdoviridae. There are currently various endemic viral disease in West Africa, such as Dengue, Ebola, Lassa, CCHF and others. There are no known drugs or cures, which have been FDA approved, and/or tested properly in humans.

There therefore remains an urgent need to find reliable methods for predicting, diagnosing and effective products for treating viral diseases. These products should be adapted to treating a number of strains of the same virus. Additionally, they should be "broad spectrum" and be useful in treating viruses, whose identity is not known, genetic variants of known viral strains and mutated viral strains.

SUMMARY OF THE INVENTION

Some embodiments of the present invention are directed to the treatment of disorders and diseases. More particularly, the disorders and diseases may be of an unknown cause, or they may be viral disorders and diseases.

There is thus provided according to an embodiment of the present invention, a compound adapted to reduce a load of an RNA virus by at least 50%, the virus causing a pathogenic disease in a mammalian subject, the compound adapted to inhibit the formation of S-adenosyl methionine (SAM) in the virus, the compound being a DOT1L inhibitor, wherein the compound has a molecular weight of less than 1000, and a therapeutic index (TI=LD.sub.50:ED.sub.50) greater than 30 in the mammalian subject.

Additionally, according to an embodiment of the present invention, the RNA virus is Ebola virus.

Furthermore, according to an embodiment of the present invention, the compound is EPZ5676.

Moreover, according to an embodiment of the present invention, there is provided a pharmaceutical composition including at least one compound as described herein.

Additionally, according to an embodiment of the present invention, the pharmaceutical composition includes two compounds.

Importantly, according to an embodiment of the present invention, the pharmaceutical composition includes an SAHH inhibitor and a DOT1L inhibitor.

Further importantly, according to an embodiment of the present invention, the pharmaceutical composition includes CAC3ADO and EPZ5676.

Yet further importantly, according to an embodiment of the present invention, the pharmaceutical composition includes DDFA and EPZ5676.

Yet further, according to an embodiment of the present invention, the pharmaceutical composition includes DDFA and SGC 0946.

Additionally, further, according to an embodiment of the present invention, the pharmaceutical composition includes DDFA and EPZ004777.

Additionally, further, according to an embodiment of the present invention, the pharmaceutical composition includes CAC3ADO and SGC 0946.

Moreover, according to an embodiment of the present invention, the virus is Ebola virus.

Notably, according to an embodiment of the present invention, the pathogenic disease is a hemorrhagic disease.

Additionally, according to an embodiment of the present invention, the pharmaceutical composition further includes at least one α-glucosidase inhibitor.

Additionally, according to an embodiment of the present invention, the pharmaceutical composition further includes at least one cathepsin B inhibitor.

Yet further, according to an embodiment of the present invention, the pharmaceutical composition further includes at least one endothelial barrier enhancer.

Additionally, according to an embodiment of the present invention, the pharmaceutical composition further includes at least one TNF alpha inhibitor.

Moreover, according to an embodiment of the present invention, the pharmaceutical composition further includes at least one collagen precursor.

Furthermore, according to an embodiment of the present invention, the pharmaceutical composition further includes at least one folate remover.

Additionally, according to an embodiment of the present invention, the RNA virus is Ebola virus and the composition includes;

a) an S-adenosyl homocysteine hydrolase (SAHH) inhibitor and a DOT1L inhibitor; and
b) at least one TNF alpha inhibitor; and optionally at least one of;
   i. at least one α-glucosidase inhibitor;
   ii. at least one endothelial barrier enhancer;
   iii. at least one cathepsin B inhibitor; and
   iv. at least one collagen precursor.

There is thus provided according to another embodiment of the present invention, use of a compound as described herein, in the preparation of a medicament suitable for administration to a human in a pharmaceutically effective amount, wherein the medicament is suitable for treating a pathogenic disease or disorder in the human.

There is thus provided according to another embodiment of the present invention, a method for reducing a load of an infectious RNA virus causing a pathogenic disease in a mammalian subject, the method including administering to the subject the compound, as described herein.

There is thus provided according to another embodiment of the present invention, a method for reducing a load of an infectious RNA virus causing a pathogenic disease in a mammalian subject, the method including administering to the subject the pharmaceutical composition as described herein.

There is thus provided according to another embodiment of the present invention, a method for reducing a load of a Filovirus causing a hemorrhagic disease in a mammalian subject, the method including administering to the subject the pharmaceutical composition as described herein.

Additionally, according to an embodiment of the present invention, the composition is further effective to enhance endothelial barrier integrity.

Furthermore, according to an embodiment of the present invention, the composition is further effective to enhance collagen generation in the subject.

Yet further, according to an embodiment of the present invention, the compound is selected from compounds listed in table 1.

Additionally, according to an embodiment of the present invention, the pharmaceutical composition includes any combination of compounds in table 1 in a pharmaceutically effective amount.

The present invention provides compositions for reducing a load of an infectious agent causing a pathogenic disease in a mammalian subject, the composition including at least one product (d1, d2, . . . $d_N$) in a pharmaceutically effective amount ($ED_{XX}$), wherein ED is an effective dose and XX is the percentage reduction of the load, wherein each of the at least one product is effective to inhibit at least one step (s1, s2, . . . sN) in a pathway associated with replication of the infectious agent to reduce the load, $N_0$ of the infectious agent in the subject to a final number at time t, $N_t$, wherein a ratio of the load $N_0$ to the final number $N_t$ is sufficiently large to provide the subject with a high statistical probability to survive the disease.

There is thus provided according to an embodiment of the present invention, a pharmaceutical composition for reducing a load of an infectious agent causing a pathogenic disease in a mammalian subject, the composition including; at least one product (d1, d2, . . . $d_N$) in a pharmaceutically effective amount ($ED_{XX}$), wherein ED is an effective dose and XX is the percentage reduction of the load, wherein each of the at least one product is effective to inhibit at least one step (s1, s2, . . . sN) in a pathway associated with replication of the infectious agent to reduce the load, $N_0$ of the infectious agent in the subject to a final number at time t, $N_6$ wherein a ratio of the load $N_0$ to the final number $N_t$ is sufficiently large to provide the subject with a high statistical probability to survive the disease.

Additionally, according to an embodiment of the present invention, the infectious agent is selected from the group consisting of a virus, a bacterium, a fungus, a parasite and combinations thereof.

Furthermore, according to an embodiment of the present invention, the infectious agent is a virus.

Further, according to an embodiment of the present invention, the virus is an RNA virus.

Yet further, according to an embodiment of the present invention the RNA virus is selected from families Arenaviridae, Filoviridae, Bunyaviridae, Flaviviridae, and Rhabdoviridae.

Moreover, according to an embodiment of the present invention, the virus is Ebola virus.

Additionally, according to an embodiment of the present invention, the pathogenic disease is a hemorrhagic disease.

It should be noted that, according to an embodiment of the present invention, the disease has a survival rate of less than 60%.

Notably, according to an embodiment of the present invention, the pharmaceutical composition includes at least one S-adenosyl homocysteine hydrolase (SAHH) inhibitor.

Furthermore, according to an embodiment of the present invention, the pharmaceutical composition includes at least one α-glucosidase inhibitor.

Further, according to an embodiment of the present invention, the pharmaceutical composition includes at least one cathepsin B inhibitor.

Importantly, according to an embodiment of the present invention, the pharmaceutical composition includes at least one endothelial barrier enhancer.

Additionally, according to an embodiment of the present invention, the pharmaceutical composition includes at least one TNF alpha inhibitor.

Moreover, according to an embodiment of the present invention, the pharmaceutical composition includes at least one NF kappa B inhibitor.

Additionally, according to an embodiment of the present invention, the pharmaceutical composition includes at least one TNF alpha inhibitor.

Furthermore, according to an embodiment of the present invention, the pharmaceutical composition includes at least one collagen precursor.

Additionally, according to an embodiment of the present invention, the pharmaceutical composition includes at least one DOT1L inhibitor.

Further, according to an embodiment of the present invention, the pharmaceutical composition includes at least one folate remover.

Notably, according to an embodiment of the present invention, the infectious agent is Ebola virus and the composition includes;

a) at least one of an S-adenosyl homocysteine hydrolase (SAHH) inhibitor or a DOT1L inhibitor; and
b) at least one TNF alpha inhibitor; and optionally at least one of;
   i. at least one α-glucosidase inhibitor;
   ii. at least one endothelial barrier enhancer;
   iii. at least one cathepsin B inhibitor; and
   iv. at least one collagen precursor.

Additionally, according to an embodiment of the present invention, each of the inhibitors, enhancers and precursors has a therapeutic index of more than 30.

Importantly, according to an embodiment of the present invention, each of the inhibitors, enhancers and precursors has a therapeutic index of more than 50.

Further, according to an embodiment of the present invention, at least one of the inhibitors, enhancers and precursors has a therapeutic index of more than 100. Additionally, according to an embodiment of the present invention, at least one of the inhibitors, enhancers and precursors is a generally regarded as safe (GRAS) product.

Furthermore, according to an embodiment of the present invention, some of the inhibitors, enhancers and precursors is a generally regarded as safe (GRAS) product.

Further, according to an embodiment of the present invention, each of the inhibitors, enhancers and precursors is a generally regarded as safe (GRAS) product.

Additionally, according to an embodiment of the present invention, each at least one of the inhibitors, enhancers and precursors is an FDA approved drug for a first indication and the pathogenic disease is a second indication.

Most importantly, according to an embodiment of the present invention, the composition does not require FDA approval.

Usefully for Africa, according to an embodiment of the present invention, the composition costs less than $100 for the effective dose.

Additionally, according to an embodiment of the present invention, the pharmaceutical composition includes;

a) Vitamin C;
b) Bioavailable curcumin;
c) at least one SAHH inhibitor; and
d) at least one cathepsin B inhibitor.

Additionally, according to an embodiment of the present invention, the pharmaceutical composition further includes at least one anti-retroviral drug. Further, according to an embodiment of the present invention, the pharmaceutical composition further includes at least one analgesic.

Moreover, according to an embodiment of the present invention, the pharmaceutical composition further includes at least one of creatine, Coenzyme Q10, Ginseng, and N-acetyl-L cysteine; glutathione, alpha lipoic acid, ajoene, allicin, limonene, Coenzyme Q10, quercetin, N-acetyl-L cysteine, reservatrol, and lycopene; choline and carnitine.

Furthermore, according to an embodiment of the present invention, the composition is liquid.

Additionally, according to an embodiment of the present invention, the composition is solid.

Notably, according to an embodiment of the present invention, the composition is suitable for oral, parenteral, transdermal, intra-venous or intra-muscular administration.

Additionally, according to an embodiment of the present invention, the composition is a slow-release composition.

Moreover, according to an embodiment of the present invention, the slow release composition is formulated for provision by at least one of an intravenous drip, a transdermal device and a slow-release oral formulation.

Importantly, according to an embodiment of the present invention, $N_t$ is less than or equal to $N_0\times(\Sigma\{(1-_{XX/100})_{d1}\times(1-_{XX/100})_{d2} \ldots \times(1-_{XX/100}))_{dn})\}$ for at least one of the steps (s1, s2, . . . sN) s1 to sN.

Additionally, according to an embodiment of the present invention, $N_t$ is less than or equal to $N_0\times(\Sigma\{(1-_{XX/100})_{d1}\times(1-_{XX/100})_{d2} \ldots \times((1-_{XX/100}))_{dn})\}$ for at least two of the steps (s1, s2, . . . sN) s1 to sN.

Moreover, according to an embodiment of the present invention, $N_t$ is less than or equal to $N_0\times(\Sigma\{(1-_{XX/100})_{d1}\times(1-_{XX/100})_{d2} \ldots \times((1-_{XX/100}))_{dn})\}$ for at least three of the steps (s1, s2, . . . sN) s1 to sN.

Furthermore, according to an embodiment of the present invention, $N_t$ is less than or equal to $N_0\times(\Sigma\{(1-_{XX/100})_{d1}\times(1-_{XX}/100)_{d2} \ldots \times((1-_{XX/100}))_{dn})\}$ for at least three of the steps (s1, s2, . . . sN) s1 to sN.

Additionally, according to an embodiment of the present invention, $N_t$ is less than or equal to $N_0\times(\Sigma\{(1-_{XX/100})_{d1}\times(1-_{XX}/100)_{d2} \ldots \times((1-_{XX/100}))_{dn})\}$ for at least four of the steps (s1, s2, . . . sN) s1 to sN.

There is thus provided according to another embodiment of the present invention, use of a pharmaceutical composition, as described herein, in the preparation of a medicament suitable for administration to a human in a pharmaceutically effective amount, wherein the medicament is suitable for treating a pathogenic disease or disorder in the human.

There is thus provided according to an additional embodiment of the present invention, a method for predicting efficacy of a pharmaceutical composition in reducing a load of an infectious agent causing a pathogenic disease in a mammalian subject, the method including determining for at least one product (d1, d2, . . . $d_N$) an effective dose ($ED_{XX}$), wherein ED is an effective dose and XX is the percentage reduction of the load, wherein each of the at least one products is effective to inhibit at least one step (s1, s2, . . . sN) in a pathway associated with replication of the infectious agent to reduce the load, $N_0$ of the infectious agent in the subject to a final number at time t, $N_t$, wherein a ratio of the load $N_0$ to the final number $N_t$ is sufficiently large to provide the subject with a high statistical probability to survive the disease; and wherein the pharmaceutical composition includes the at least one products in the effective dose.

Additionally, according to another embodiment of the present invention, in the method, $N_t$ is less than or equal to $N_0\times(\Sigma\{(1-_{XX/100})_{d1}\times(1-_{XX}/100)_{d2} \ldots \times((1-_{XX/100}))_{dn})\}$ for at least one the step (s1, s2, . . . sN) s1 to $S_N$.

There is thus provided according to another embodiment of the present invention, a method for reducing a load of an infectious agent causing a pathogenic disease in a mammalian subject, the method including administering to the subject the pharmaceutical composition as described herein.

Additionally, according to an embodiment of the present invention, the infectious agent is a virus and the composition includes;

a) at least one cathepsin B inhibitor; and b) at least one TNFα inhibitor.

Further, according to an embodiment of the present invention, the infectious agent is a virus and the composition includes;

a) at least one cathepsin B inhibitor; and b) at least one S-adenosyl homocysteine hydrolase (SAHH) inhibitor.

Yet further, according to an embodiment of the present invention, the infectious agent is a virus and the composition includes;

a) at least one S-adenosyl homocysteine hydrolase (SAHH) inhibitor.

b) at least one TNFα inhibitor.

Additionally, according to an embodiment of the present invention, the infectious agent is Ebola virus and the composition includes;

a) at least one cathepsin B inhibitor; and b) at least one S-adenosyl homocysteine hydrolase (SAHH) inhibitor.

Importantly, according to an embodiment of the present invention, the infectious agent is Ebola virus and the composition includes;

a) at least one cathepsin B inhibitor; and b) at least one S-adenosyl homocysteine hydrolase (SAHH) inhibitor; and c) a DOT1L inhibitor.

There is thus provided according to another embodiment of the present invention, a method for reducing a load of a Filovirus causing a pathogenic disease in a mammalian subject, the method including administering to the subject the pharmaceutical composition as described herein.

There is thus provided according to another embodiment of the present invention, a method for reducing a load of a Filovirus causing a pathogenic disease in a mammalian subject, the method including administering to the subject the pharmaceutical composition as described herein, wherein the composition is further effective to reduce a load of inflammatory cytokines from an initial load $ICY_0$ to a final load at time t, $ICY_t$, wherein a ratio of $ICY_0$ to $ICY_t$, is sufficiently large to provide the subject with a very high statistical probability to survive the disease.

Additionally, according to an embodiment of the present invention, the composition is further effective to enhance endothelial barrier integrity.

Furthermore, according to an embodiment of the present invention, the composition is further effective to enhance collagen generation in the subject.

According to some additional embodiments of the present invention, the pharmaceutical composition is liquid. In other cases, it is solid. In yet further cases, it is a suspension.

According to some additional embodiments of the present invention, the composition is a slow-release composition.

According to some further embodiments of the present invention, the slow release composition is formulated for provision by at least one of an intravenous drip, a transdermal device and a slow-release oral formulation.

According to some yet further embodiments of the present invention, the pharmaceutical composition further includes at least one neuro-protective agent.

There is thus provided according to some additional embodiments of the present invention, a use of a pharmaceutical composition as described herein in the preparation of a medicament suitable for administration to a human in a pharmaceutically effective amount, wherein the medicament is suitable for treating a disease or disorder in the human.

According to further embodiments, the disease is a viral disease.

DETAILED DESCRIPTION OF PREFERRED EMBODIMENTS

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

Over the first few days post infection, an Ebola virus multiplies from around a few hundred plaque forming units (PFUs) introduced into a subject at time zero to tens of thousands—many million/billion PFUs (Sanchez et al., 2004). It has been reported that the average or mean replication rate line, leading to fatalities were several orders of magnitude greater than that in surviving hosts (Sanchez et al., 2004) having a mean PFU value of a significantly lower log slope than that of the fatal cases. For example, at day 4, post-infection, the non-survivors (fatalities) have a mean PFU count/ml 256 of $10^8$ (100 million viruses/ml) and the survivors' mean PFU/ml count 266 is only around $3\times10^4$ (30,000 viruses/ml). Thus a ratio $R_{FS}$ of the mean number of PFUs/ml in fatalities at time $t=N_{TF}$ to the mean number of PFUs/ml in fatalities at time $t=N_{T}s$ is around 3333. This ratio $R_{FS}$ is typically in the range of 10-100000, more typically in the range of 50-50000. Generally, one can state that $1<R_{FS}<10000$ for Ebola.

A statistical solution for improving survival rates would therefore be to reduce the viral load at time t, by at least 10, at least 100 and more preferably by at least 1000 and most preferably by at least 10000 fold. After three days, for example, the ratio $R_{FS}$ is around $(2\times10^5)/(7\times10^3)=28.6$. After two days, the ratio is less than ten.

This graph shows the importance of early treatment. In other words, to provide a potential "fatality" with a given treatment three days post infection may be 3333/28.7=116.5, at least one hundred times more effective than at day four. Providing a treatment at day two may be 3333/10=333 times as effective in saving the person's life, than at day four. Thus, non-confirmed suspected cases of infection should be treated before the lab results are received.

In order to inhibit Ebola virus replication, several steps in its replication cycle should be inhibited. This method applies, at least in part, to all viruses, bacterial, fungal, parasitic infections, and is exemplified with respect to Ebola virus for the sake of simplicity.

In order to inhibit viral replication, at least one of the replication steps 1, 2, 3, 4, 5, 6, 7 and 8 of viral replication needs to be inhibited (respectively, cathepsin B or L inhibitors, folate receptor inhibitors, SAHH inhibitors, alpha glucosidase inhibitors, RNA synthesis inhibitors, RNA reverse transcription inhibitors, protein synthesis inhibitors, viral cap formation inhibitors and translation inhibitors). More preferably, in order to inhibit viral replication, at least two of the schematic steps 1, 2, 3, 4, 5, 6, 7 and 8 of viral replication need to be inhibited. Yet more preferably, in order to inhibit viral replication, at least three of the schematic steps 1, 2, 3, 4, 5, 6, 7 and 8 of viral replication need to be inhibited. Even more preferably, in order to inhibit viral replication, at least four of the schematic steps 1, 2, 3, 4, 5, 6, 7 and 8 of viral replication need to be inhibited. Yet even more preferably, in order to inhibit viral replication, at least five of the schematic steps 1, 2, 3, 4, 5, 6, 7 and 8 of viral replication need to be inhibited.

In order to quantify a predicted inhibition of viral replication and reduction in the viral load, the following steps are performed in the method of the present invention.

a) Identify replication steps of a pathogen.

b) For at least one of the schematic steps 1, 2, 3, 4, 5, 6, 7 and 8 listed hereinabove, identify at least one inhibitor with a published and known effective dosage, such as ED50, the effective dose to inhibit 50% of the target pathogen (virus in this case). Some non-limiting examples appear in Table 1 hereinbelow.

c) Calculate predicted combination therapy viral load reductions as follows:— i. For each step 1, 2, 3, 4, 5, 6, 7 and 8 (also termed $S_1$, $S_2$ . . . $S_N$ herein) calculate, for each candidate drug/compound/effector/agent, a reduction in the viral load anticipated by that drug/compound in a given amount. For example, if the 3-DEAZANEPLANOCIN A known $ED_{50}$ is 2 μM and the $ED_{80}$ is 4 μM, then the residual viral load after treatment is the initial load $N_0$ multiplied by the reduction in load. For example, if the initial load $N_0$ of Ebola virus is $10^5$ PFU/ml and an effective dose of 3-DEAZANEPLANOCIN is provided such that the in vivo concentration thereof is 2 μM, then the final load $N_t$ at a time after administration of the 3-DEAZANEPLANOCIN $N_t=N_0\times(1-(ED50/100)=(1-0.5)=0.5\times10^5$ PFU/ml at 4 μM and $(1-0.8)=2\times10^4$ at 4 μM.

ii. If the drugs/compounds combined are on different steps (or pathways) 1, 2, 3, 4, 5, 6, 7 and 8, then assume (this is a preliminary assumption until practical kinetic values can be obtained-see Chou and Talalay, 1984, for a full mathematical analysis) that combining them produces a combination effect. Thus, at least as a first estimate, the values of $N_t$ are assumed to be a multiple of each Nt calculated alone.

For example 4 μM 3-DEAZANEPLANOCIN+0.004 g BETA-OLEANOLIC ACID (B.O.A) ($ED_{50}$) for Cathepsin B, provides an $ED_{80}$ and $N_t$ 3-deaz xB.O.A$=N_0\times(1-0.8)(1-0.5)=10000$—reducing the viral load 10 fold.

Thus, for example a combination of 4 μM 3-DEAZANEPLANOCIN+0.004 g BETA-OLEANOLIC ACID (ED50) for Cathepsin B+ MIGLUSTAT 2 g/day (ED50) would provide a theoretical 20 fold reduction in the viral load.

The combinations of similar drugs working at the same step on the same active site in an enzyme cannot be fully predicted without experimentation (Chou et al., 1984) but may be additive. This may also depend on if they are provided at the same time or at different times.

According to some embodiments, for the sake of simplicity, it is assumed that a combination of two drugs working on the same enzyme is combinatory (multiplied). For example a combination of adenosine 4.2 g/day for 70 kg person provides its $ED_{50}$, then the residual viral load for adenosine alone is $(1-0.5)=0.5$ and if 3-DEAZANEPLANOCIN (C3-NPC-A) is used at 4 μM and adenosine at 4.2 g/day, the statistical combined residual viral load is ((1−0.8)×(1−0.5))=0.2×0.5=0.1×original viral load. Thus, this combination of only two compounds working on only one of the steps (step 2 in this case) of steps s1, s2, s3, s4, s5, s6, s7 and s8 in FIG. 2B, would be sufficient to "move the patient from the fatalities curve 252 to the survivors' curve 262, if treated before or on day two. It would not be sufficient on day three or four.

For each pathway, such as inhibiting 2 by s-adenosyl homocysteine hydrolase (SAHH) E.C. 3.3.1.1. inhibitors, a sum of the combination therapies to be used on that pathway, using drugs or products $d_1$, $d_2$ to $d_n$ $$\Sigma\{(1-ED_{XX})_{d1}\times(1-ED_{XX})_{d2}\times((1-ED_{XX})_{dn})\}s_2 \ldots$$

Thus, in the example above this would lead to a ten-fold reduction in viral load.

However, if these two drugs were provided with 32.85 mg (this value needs to be verified) of MIGLUSTAT, which is an ED50 for viral integration pathways, and 0.185 mg of berberine and 0.03 g of quercetin, both inhibitors of step 1B, then the reduction in the viral load would be 0.1×0.5×0.5×0.5=0.0125 of the initial viral load, or roughly a hundred-fold reduction in the viral load. This could be applied on day three successfully.

All these calculations assume that the literature provided and published is reliable and accurate.

A partially effective combination on day four would be the five drugs/compounds, as above with a combination of 0.004 g beta-oleanolic acid and 0.2 g beta-ursolic acid+ viral load reduction=0.0125×0.5×0.5=0.003125. This would mean that the treated person would have 10 times more PFUs/ml than the mean survivor and this may/may not be sufficient to save him/her.

Additionally or alternatively, it has been found that Ebola patients have increased loads of inflammatory cytokines, leading to reduced endothelial barrier integrity, leading to hemorrhage. Thus there is a further/alternative requirement to reduce a load of inflammatory cytokines from an initial load $ICY_0$ to a final load at time t, $ICY_t$, wherein a ratio of $ICY_0$ to $ICY_t$, is sufficiently large to provide the subject with a very high statistical probability to survive the disease. Collagen precursors may also be effective in "plugging the holes" in the endothelial barrier.

The data provided in Table 1 could optionally be optimized using mathematical methods, known in the art to minimize at least one of cost, minimizing the number of drugs, possible drug combination reactions etc.

In bacterial and other pathogenic models other pathogenic replication steps would be required, as are known in the art.

In order to avert the requirement for lengthy FDA approval, over-the-counter drugs or compounds, which are GRAS (generally regarded as safe) should be used to treat Ebola.

Lu et al., (2010) describes a method (prior art) for preventing pulmonary edema of by improving endothelial barrier function, incorporated herein by reference.

The methods of the present invention include methods for improving endothelial layer integrity after an Ebola virus infection, in accordance with an embodiment of the present invention. According to published literature (Baize et al., 2002), Ebola viruses infiltrate monocytes forming infected monocytes. Infected monocytes release massive amounts of inflammatory cytokines damaging endothelial cells on a barrier. The endothelial cells die forming dead endothelial cells and inducing vascular shock to the infected organism/host. This vascular shock and perturbation of endothelial cell barriers can be reduced by step 9—providing endothelial cell enhancers/barrier integrity enhancers (see table 1 hereinbelow) and/or providing natural TNFalpha inhibitors to reduce the cytokine load/storm made by the infected monocytes. Some non-limiting examples of TNFalpha inhibitors known in the art are, curcumin, fisetin, genistein, resveratrol and capsaicin (see Habtemariam, 2000, incorporated herein by reference).

The present invention provides a method for increasing homocysteine in a patient, in accordance with an embodiment of the present invention. S-adenosyl-methionine (SAM) is a cofactor for viral methyltransferase (Huggins et al., 1999). Thus, for Ebola patients, every effort should be made to reduce the level of SAM (for at least the first week after infection) and reduce the SAM:SAH ratio. Exactly the opposite holds for reducing hypertension and hyperhomocysteinemia. There, the aim is to increase the SAM and reduce the SAH and homocysteine. In Ebola/Marburg/Dengue/others, the aim is to work in exactly the opposite direction to alleviate hypotension and to reduce SAM, while increasing SAH. This should reduce the viral replication rate.

Thus, it would appear that Ebola patients should not be given folic acid, vitamin B12, vitamin B6, meat, or any other precursors of SAM, during the critical first days/weeks post-infection. Medical authorities should be consulted on the wisdom of providing multivitamins containing high levels of folic acid and B12 (this might be counter-productive and may increase the viral load). In other words, if a multivitamin is provided, it should be with low/no folic acid, B6 and B12. Additionally or alternatively, any suitable methyltransferase enzyme (EC.2.1.1) inhibitor may be used to reduce the viral load to prevent methylation of the viral RNA, protein, glycoprotein or other viral components. Some non-limiting examples of these enzymes to be inhibited include 2.1.1.10 homocysteine S-methyltransferase, 2.1.1.43 histone-lysine N-methyltransferase and 2.1.1.56 mRNA (guanine-N7-)-methyltransferase. Some non-limiting examples of methyl transferase inhibitors appear in Table 1 hereinbelow.

Preferably, the methyltransferase inhibitor is operative to reduce the viral load inside a mammalian or other host. According to some embodiments, the inhibitor(s) may be an s-adenosylmethionine (SAM) analog and/or competitive inhibitor of a methyl transferase enzyme, adapted to receive a methyl group from SAM.

Another point to consider is that folate receptor alpha is reported to be a cofactor for cellular entry of Marburg and Ebola viruses (Chan et al., 2001), thus, according to another embodiment of the present invention, a folate removing substance is provided to subjects infected with Ebola virus. One non-limiting example of such a substance is EGCG (epigallocatechin-3 gallate)—see Alemdaroglu et al., 2007 (IC 50 34.8 μmole/l). Harrington et al., 2004 show that homocysteine and adenosine blunt barrier dysfunction and Rho activation. Vitamin C, ornithine and arginine are all documented as being collagen precursors (see table 1 hereinbelow). It is reported that Ebola patients experience severe internal hemorrhage, possibly due to lack of collagen precursors and/or endothelial barrier dysfunction. It is therefore suggested that collagen precursors should be provided in effective amounts to reduce hemorrhage. According to some embodiments, vitamin C is provided in a megadose (see Salom, Hugo Mario Galindo, 2008). It is possible that large doses of vitamin C would be effective in reducing viral loads, too (see Smith, Lendon H., 1988).

TABLE 1

EXEMPLARY CANDIDATE COMPOUNDS USEFUL IN THE TREATMENT OF EBOLA AND OTHER VIRAL DISEASES

| COMPOUND NAME | CAS NO. | FUNCTION | ED50 | LD50 | TI | SUGGESTED DAILY DOSAGE G/70 KG ADULT | REFERENCE |
|---|---|---|---|---|---|---|---|
| VITAMIN C | 50-81-7 | TNF ALPHA INHIBITOR NKAPPAB PATHWAY INHIBITOR ANTIVIRAL COLLAGEN PRECURSOR | 29-60 MG/KG | 11,900 mg/kg 833 G | 198 | 4 G/DAY | Bowie et al. , 2000 Hemila, 1990 |
| CURCUMIN | 458-37-7 | TNF ALPHA INHIBITOR NKAPPAB PATHWAY INHIBITOR ANTIVIRAL Blocker of sepsis-induced muscle proteolysis | 29-60 MG/KG | 2000 mg/kg 140 G | 33-66 | 2 G/DAY | Anand et al. , 2007 Poylin et al, 2007 |
| INOSINE | 58-63-9 | S-ADENOSYL HOMOCYSTEINE HYDROLASE (SAHH) WEAK INHIBITOR | 29-60 MG/KG | 25000 mg/kg. 1750 G | >417 | 4 G/DAY | UELAND 1982 |
| ADENOSINE | 58-61-7 | S-ADENOSYL HOMOCYSTENE HYDROLASE (SAHH) INHIBITOR ENDOTHELIAL BARRIER ENHANCER | 29-60 MG/KG | 20000 Mg/Kg 1400 G | >333 | 4 G/DAY | UELAND 1982 LU ET AL. , 2010 Harrington et al. , 2004 |
| 3-deaza-adenosine | 6736-58-9 | SAHH INHIBITOR | 1-6 μM | 195 μM >33 MW266 | | | UELAND 1982 Djurhuus et al. , 1989 |
| ADENOSINE MONO-PHOSPHATE | 61-19-8 | S-ADENOSYL HOMOCYSTEINE HYDROLASE (SAHH) WEAK INHIBITOR | | 2900 mg/kg | | | UELAND 1982 |
| S-ADENOSYL HOMO-CYSTEINE (SAH) | 979-92-0 | S-ADENOSYL HOMOCYSTEINE HYDROLASE (SAHH) INHIBITOR | 300 μM | 890 g/kg Mw = 3842.3223 LD50, mol/kg ??? | High?? | | RADEKE ET AL, 1999 |
| S-INOSYL HOMO-CYSTEINE (SIH) | | (SAHH) WEAK INHIBITOR | | | | | |
| COMPOUND NAME | CAS NO. | FUNCTION | ED50 | LD50 | TI | SUGGESTED DAILY DOSAGE G/70 KG ADULT | REFERENCE |
| 5' DEOXY ADENOSINE | 4754-39-6 | (SAHH) INHIBITOR | 0.050 mM | ???? | ???? | | |
| | 71678-03-0 | S-ADENOSYL HOMOCYSTEINE HYDROLASE (SAHH) INHIBITOR | 20 μM-0.050 mM | LD50 of 0.29 μg mL | ???? | | RADEKE ET AL, 1999 |

TABLE 1-continued

EXEMPLARY CANDIDATE COMPOUNDS USEFUL IN THE TREATMENT OF EBOLA AND OTHER VIRAL DISEASES

| COMPOUND NAME | CAS NO. | FUNCTION | ED50 | LD50 | TI | SUGGESTED DAILY DOSAGE G/70 KG ADULT | REFERENCE |
|---|---|---|---|---|---|---|---|
| ADENOSYL DIALDEHYDE (AD) | 39798-19-1 | (SAHH) INHIBITOR | 125 µM | 6250 µM | >50 | | O'dea 1987 p3656 |
| NEPLA NOCINA | 72877-50-0 | (SAHH) INHIBITOR | 0.02-7 µG/ML | 2.7-400 | 40-500 | | DE CLERCQ 1989, 1985 |
| 3-DEAZA NEPLA NOCINA C3-NPC-A | 102052-95-9 | (SAHH) INHIBITOR | 0.04<br>400 µG/ML<br>2 µM | 400<br>1700 µM | 1-10000<br>(ROTA VIRUS)<br>850 | | Bray et al. , 2000<br>DE CLERCQ 1989, 1985<br>HUGGINS ET AL, 1999 |
| SINEFUNGIN | 58944-73-3 | A) VIRION MRNA METHYL TRANSFERASE<br>B) (SAHH) WEAK INHIBITOR | A) NANO MOLAR<br>B) 10 µM 4 mg/kg body weight/day | 50X | $423/GRAM<br>$160000/MOL<br>MW 38150 | | UELAND 1982<br>AVILA ET AL, 1990 |
| COMPOUND NAME | CAS NO. | FUNCTION | ED50 | LD50 | TI | SUGGESTED DAILY DOSAGE G/70 KG ADULT | REFERENCE |
| N-B-DEOXY-NOJIR-IMYCIN MIGLUSTAT 219 MW | 72599-27-0 | α-glucosidase inhibitor | 150 µM<br>3 mg/kg body weight to 30 mg/kg body<br>32.85 mg | Mw2192.1203<br>LD50, mol/kg,<br>LD50 1,300 mg kg-1(oral, rat) 91 g | >15476<br>2733 | 33 mg-2 g/day | Chang et al 2013<br>U.S. Pat. No. 4,849,430<br>U.S. Pat. No. 8,097,728<br>Patented in USA only |
| methyl deoxy NOJIRI-MYCIN | 69567-10-8 | α-glucosidase inhibitor | | | | | U.S. Pat. No. 4,849,430<br>Chang et al 2013 |
| ARISTO-MYCIN roxithromycin CaAdo | 80214-83-1 | S-ADENOSYL HOMOCYSTEINE HYDROLASE (SAHH) INHIBITOR | 4 µM | 30 µM | 8 | | HUGGINS ET AL, 1999 |
| s-carboxybutyl DL homo-cysteine | 88096-03-1 | (SAHH) INHIBITOR | | LD50<br>500 mg/kg | | | |
| CA-C3-ADO 3-deaza-adenosine | 6736-58-9 | S-ADENOSYL HOMOCYSTEINE HYDROLASE (SAHH) INHIBITOR | 1.4<br>30 µM | 100<br>5640 µM | 70<br>188 | | DE CLERCQ 1989,<br>HUGGINS ET AL, 1999 |
| DDFA MW 287 5'-deoxy-5'-difluoro-adenosine | 131077-98-0 | S-ADENOSYL HOMOCYSTEINE HYDROLASE (SAHH) INHIBITOR | 54 | 13,900 | 257 | | HUGGINS ET AL, 1999 |
| QUERCETIN MW 302 | 117-39-5 | (CAT B) CATHEPSIN B INHIBITOR<br>Vp30 activator inhibitor | IC50<br>11 µM<br>0.03 g | Oral LD50 (rat): 161 mg/kg<br>11.27 g | 376 | 0.03 g/day | CHANDRAN ET AL., 2005<br>JEDINAK ET AL. , 2006<br>Kasmi 2014 |
| BERBERINE MW 336 | CasNo-2086-83- 1 Berberine hydrochloride (CAS 633-65-8), CAS No. 2086-83-1 | (CAT B) CATHEPSIN B INHIBITOR | IC50<br>550 µM<br>0.185 g/day | Oral LD50 (mouse): >29,586 mg/kg;<br>2072 g | 11200 | 0.185 g/day | CHANDRAN ET AL. , 2005<br>JEDINAK ET AL. , 2006 |

TABLE 1-continued

EXEMPLARY CANDIDATE COMPOUNDS USEFUL IN THE TREATMENT OF EBOLA AND OTHER VIRAL DISEASES

| COMPOUND NAME | CAS NO. | FUNCTION | ED50 | LD50 | TI | SUGGESTED DAILY DOSAGE G/70 KG ADULT | REFERENCE |
|---|---|---|---|---|---|---|---|
| COMPOUND NAME | CAS NO. | FUNCTION | ED50 | LD50 | TI | SUGGESTED DAILY DOSAGE G/70 KG ADULT | REFERENCE |
| BETA-OLEANOLIC ACID 457 MW | 508-02-1 | (CAT B) CATHEPSIN B INHIBITOR | IC50 9 µM 0.004 g | LD50 = >2000 mg/kg 140 g | 35000 | 0.004 g | CHANDRAN ET AL. , 2005 JEDINAK ET AL. , 2006 |
| BETA-URSOLIC ACID 457 | 77-52-1 | (CAT B) CATHEPSIN B INHIBITOR | IC50 10 µM 50 MG/KG ED50 = 3.15 µg/ml) | 8330 mg)/kg 583.1 g | 166.62916 | 0.2 g | CHANDRAN ET AL. , 2005 JEDINAK ET AL. , 2006 |
| Arginine MW 174 | 74-79-3 | COLLAGEN PRECURSOR | 2.5 g | LD50: 3600 mg/kg, 252 g | 100 | 2.5 g/day | BARBUL, 2008 |
| Ornithine MW 132 | 70-26-8 | COLLAGEN PRECURSOR | 3.5 g | 5000 mg/kg 350 g | 100 | 3.5 g/day | BARBUL, 2008 |
| VANADATE 187 | 13721-39-6 | Inhibit proteolysis (CAT B) CATHEPSIN B INHIBITOR | ED50 = 3 ± 0.7 micro M | LD50 = 330 mg/kg 23.1 g | 15400 | 0.5-1.5 mg/day | TANAKA ET AL. 1984 |
| HOMO-CYSTEINE 135 | 6027-13-0 | ENDOTHELIAL BARRIER ENHANCER | 50 µM 0.4725 g | 500 mg/kg 35 g | 74 | ?? is therapeutic window too small? | LU ET AL. , 2010 Harrington et al. , 2004 |
| EGCG (epigallo-catechin-3 gallate) MW = 458 | CAS 989-51-5 | 1) Folaet remover 2) CAT B) CAT HEPSIN B INHIBITOR 3) HSPA5ATP binding site inhibitor 4) NKAPPAB PATHWAY INHIBITOR | IC50 34.8 µmole/l 10 µg/ml | 14,500 mg/kg 1015 g | 1450 | 0.7 g/day | Alemdaroglu et al. , 2007 Khafif et al. , 1998 Gehring et al., 2014, St. Patrick Reid/Shurtleff et al, 2014 |
| EPZ-5676562.71 | 1380288-87-8 | DOT1L INHIBITOR | 3-70 nM Ki of 80 pM | | >37,000-fold? | USD 1222/50 mg | WO14100662 A1 |
| EPZ004777 Molecular Weight: 539.67 | 1338466-77-5 | DOT1L INHIBITOR | IC50 of 0.4 nM 0.015 mg | (Rat LD50 = 590 mg/kg | 39333 | $970/50 mg | BERNT ET AL. 2011 |
| SGC 0946 619 = mw | CAS 1561178-17-3 | DOT1L INHIBITOR | IC50 of 0.3 nM 0.2 µg/l 13 µg | Rat LD50 = 590 mg/kg) 41.3 g. | $3.2 \times 10^6$ | | Yu et al 2012 |
| Mycophenolic acid MW = 320.34 | 24280-93-1 ✓ | INOSINE MONO-PHOSPHATE DEHYDRO-GENASE INHIBITOR AND/OR RNA TRANSLATION, | 0.30 µM 0.10 µg/ml 7 mg | 352 mg/kg 24 g | 3428 | | Takhampunya et al. 2006 |
| Oleuropein MW = 540 | 32619-42-4 ✓ | VIRAL FUSION AND INTEGRATION Vp30 activator inhibitor | 55 nM | >10,000 nM | >181 | | Lee-Huang et al. 2007 Kasmi 2014 |
| Hydroxytyrosol MW = 154 | 10597-60-1 ✓ | VIRAL FUSION AND INTEGRATION | 61 nM | >10,000 nM | >164 | | Lee-Huang et al. 2007 |
| SGI-110557.4 | 929901-49-5 | DNA METHYLATION INHIBITOR | 438 nM | | | | Covre et al, 2013 |
| UNC0631635.9. | 1320288-19-4 | G9a/GLP-mediated dimethylation of histone 3 on lysine 9 | IC50 = 4 nM | 2 mg/kg | 1000? | | Zagni, ET AL. , 2013 |

TABLE 1-continued

EXEMPLARY CANDIDATE COMPOUNDS USEFUL IN THE TREATMENT OF EBOLA AND OTHER VIRAL DISEASES

| COMPOUND NAME | CAS NO. | FUNCTION | ED50 | LD50 | TI | SUGGESTED DAILY DOSAGE G/70 KG ADULT | REFERENCE |
|---|---|---|---|---|---|---|---|
| UNC0646621.9 | 1320288-17-2 | Potent and selective inhibitor of the homologous protein lysine methyltransferases, | IC50 values are 6 nM and 15 nM for G9a and GLP, respectively). | low cellular toxicity (EC50 = 4.7 μM in MCF7 cells | 130-510 | | Liu et al. , 2011 |
| Kaemferol Mw = 286 | 520-18-3 | Vp30 activator inhibitor | 12.6 and 25.9 nM against JEV | 2.17 g/kg | ? | | Kasmi 2014 |
| EPZ6438572 | 1403254-99-8 | Protein methyltransferase inhibitor Pediatric use | 2.5 nM | | ? | | Knutson et al, 2013 |
| Cordycepin | CAS 73-03-0 | | | | | | |

The SAHH inhibitor may be selected from any SAHH inhibitors known in the art and/or described herein, including DDFA (Huggins et al 1999). The DOT1L inhibitors may include any DOT1L inhibitor, known in the art.

The compositions of the present invention may be provided in any suitable dosage form. These dosage forms may be injectable, infusible, inhalable, edible, oral or combinations thereof, as are known in the art. According to some embodiments, the dosage form is an oral dosage form. Oral dosage forms comprise liquids (solutions, suspensions, and emulsions), semi-solids (pastes), and solids (tablets, capsules, powders, granules, premixes, and medicated blocks).

In another embodiment, additional methods of administering the compositions of the invention comprise injectable dosage forms. In another embodiment, the injectable is administered intraperitoneally. In another embodiment, the injectable is administered intramuscularly. In another embodiment, the injectable is administered intradermally. In another embodiment, the injectable is administered intravenously. Each possibility represents a separate embodiment of the present invention.

In another embodiment, the compositions are administered by intravenous, intra-arterial, or intra-muscular injection of a liquid preparation. Suitable liquid formulations include solutions, suspensions, dispersions, emulsions, oils and the like. In another embodiment, the compositions are administered intravenously and are thus formulated in a form suitable for intravenous administration. In another embodiment, the pharmaceutical compositions are administered intra-arterially and are thus formulated in a form suitable for intra-arterial administration. In another embodiment, the compositions are administered intra-muscularly and are thus formulated in a form suitable for intra-muscular administration.

Additionally, according to some embodiments of the present invention, the at least one neuro-protective agent is provided in a pharmaceutically effective amount and wherein the at least one neuro-protective agent is selected from the group consisting of; erythropoietin, an erythropoietin derivative, an extract of at least one of; Ginko biloba; *Hydrocotyle asiatica*, St. Johns Wort, Kava Kava, Passion Flower, Skull Cap, valerian, vervain, passionflower and catnip; Omega 3, a myelin precursor, bilobide, ginsenoside, ginseng radix, Cantella asiatica, Peoniae alba, Radix paeonifloria, watermelon extract and a cantaloupe extract.

According to some additional embodiments of the present invention, the slow release formulation includes at least one of a POLYOX™, METHOCEL™ and ETHOCEL™ excipient. According to some additional embodiments of the present invention, the slow release dosage form including a pharmaceutical composition as described herein covered by at least one non-allergenic, non-prolamine polymer layer.

According to some additional embodiments of the present invention, the slow release dosage form the dosage form is non allergenic. According to some additional embodiments of the present invention, the slow release dosage form does not comprise animal matter (is vegetarian). According to some additional embodiments of the present invention, the slow release dosage form is kosher.

According to some additional embodiments of the present invention, a use of a pharmaceutical composition is provided for the preparation of a medicament suitable for administration to a human in a pharmaceutically effective amount, wherein the medicament is suitable for treating a disease or disorder in the human.

According to some additional embodiments of the present invention, the composition is suitable for oral, parenteral, transdermal, intra-venous or intra-muscular administration.

According to some embodiments, the composition is a slow-release composition. In some cases, the slow release composition is formulated for provision by at least one of an intravenous drip, a trans-dermal device and a slow-release oral formulation.

Some examples of oral dosage forms in the art include, WO90/04391, which discloses an oral dosage form of omega-3 polyunsaturated acids to overcome the problems of vascular diseases. It is known to supply said acids in soft gelatine capsule shells.

EP 2 240 581 B1 discloses a gelatine capsule for pharmaceutical use with a controlled release of active ingredients and a process for the preparation of said gelatine capsules. During said process xylose is added to the liquid gelatine from which afterwards gelatine capsules are formed. Gelatine capsules manufactured according to the process provide retarded release of active ingredients.

U.S. Pat. No. 7,264,824 discloses and oral dosage form for food and food supplements, as well as dietetics comprising polyunsaturated acids in a xylose-hardened gelatine capsule with a retarded release time. According to some embodiments of the present invention, the compositions described herein may be in a suspension or emulsion.

A suspension is a coarse dispersion of insoluble drug particles, generally with a diameter exceeding 1 μm, in a liquid (usually aqueous) medium. Suspensions are useful for administering insoluble or poorly soluble drugs/components or in situations when the presence of a finely divided form of the material in the GI tract is required. The taste of most drugs is less noticeable in suspension than in solution, due to the drug being less soluble in suspension. Particle size is an important determinant of the dissolution rate and bioavailability of drugs in suspension. In addition to the excipients described above for solutions, suspensions include surfactants and thickening agents. Surfactants wet the solid particles, thereby ensuring the particles disperse readily throughout the liquid. Thickening agents reduce the rate at which particles settle to the bottom of the container. Some settling is acceptable, provided the sediment can be readily dispersed when the container is shaken. Because hard masses of sediment do not satisfy this criterion, caking of suspensions is not acceptable.

An emulsion is a system consisting of 2 immiscible liquid phases, one of which is dispersed throughout the other in the form of fine droplets; droplet diameter generally ranges from 0.1-100 μm. The 2 phases of an emulsion are known as the dispersed phase and the continuous phase. Emulsions are inherently unstable and are stabilized through the use of an emulsifying agent, which prevents coalescence of the dispersed droplets. Creaming, as occurs with milk, also occurs with pharmaceutical emulsions. However, it is not a serious problem because a uniform dispersion returns upon shaking. Creaming is, nonetheless, undesirable because it is associated with an increased likelihood of the droplets coalescing and the emulsion breaking. Other additives include buffers, antioxidants, and preservatives. Emulsions for oral administration are usually oil (the active ingredient) in water, and facilitate the administration of oily substances such as castor oil or liquid paraffin in a more palatable form.

A paste is a 2-component semi-solid in which drug is dispersed as a powder in an aqueous or fatty base. The particle size of the active ingredient in pastes can be as large as 100 μm. The vehicle containing the drug may be water; a polyhydroxy liquid such as glycerin, propylene glycol, or polyethylene glycol; a vegetable oil; or a mineral oil. Other formulation excipients include thickening agents, cosolvents, adsorbents, humectants, and preservatives. The thickening agent may be a naturally occurring material such as acacia or tragacanth, or a synthetic or chemically modified derivative such as xanthum gum or hydroxypropylmethyl cellulose. The degree of cohesiveness, plasticity, and syringeability of pastes is attributed to the thickening agent. It may be necessary to include a cosolvent to increase the solubility of the drug. Syneresis of pastes is a form of instability in which the solid and liquid components of the formulation separate over time; it is prevented by including an adsorbent such as microcrystalline cellulose. A humectant (eg, glycerin or propylene glycol) is used to prevent the paste that collects at the nozzle of the dispenser from forming a hard crust. Microbial growth in the formulation is inhibited using a preservative. It is critical that pastes have a pleasant taste or are tasteless.

A tablet consists of one or more active ingredients and numerous excipients and may be a conventional tablet that is swallowed whole, a chewable tablet, or a modified-release tablet (more commonly referred to as a modified-release bolus due to its large unit size). Conventional and chewable tablets are used to administer drugs to dogs and cats, whereas modified-release boluses are administered to cattle, sheep, and goats. The physical and chemical stability of tablets is generally better than that of liquid dosage forms. The main disadvantages of tablets are the bioavailability of poorly water-soluble drugs or poorly absorbed drugs, and the local irritation of the GI mucosa that some drugs may cause.

A capsule is an oral dosage form usually made from gelatin and filled with an active ingredient and excipients. Two common capsule types are available: hard gelatin capsules for solid-fill formulations, and soft gelatin capsules for liquid-fill or semi-solid-fill formulations. Soft gelatin capsules are suitable for formulating poorly water-soluble drugs because they afford good drug release and absorption by the GI tract. Gelatin capsules are frequently more expensive than tablets but have some advantages. For example, particle size is rarely altered during capsule manufacture, and capsules mask the taste and odor of the active ingredient and protect photolabile ingredients.

A powder is a formulation in which a drug powder is mixed with other powdered excipients to produce a final product for oral administration. Powders have better chemical stability than liquids and dissolve faster than tablets or capsules because disintegration is not an issue. This translates into faster absorption for those drugs characterized by dissolution rate-limited absorption. Unpleasant tastes can be more pronounced with powders than with other dosage forms and can be a particular concern with in-feed powders, in which it contributes to variable ingestion of the dose. Moreover, sick animals often eat less and are therefore not amenable to treatment with in-feed powder formulations. Drug powders are principally used prophylactically in feed, or formulated as a soluble powder for addition to drinking water or milk replacer. Powders have also been formulated with emulsifying agents to facilitate their administration as liquid drenches.

A granule is a dosage form consisting of powder particles that have been aggregated to form a larger mass, usually 2-4 mm in diameter. Granulation overcomes segregation of the different particle sizes during storage and/or dose administration, the latter being a potential source of inaccurate dosing. Granules and powders generally behave similarly; however, granules must deaggregate prior to dissolution and absorption.

A premix is a solid dosage form in which an active ingredient, such as a coccidiostat, production enhancer, or nutritional supplement, is formulated with excipients. Premix products are mixed homogeneously with feed at rates (when expressed on an active ingredient basis) that range from a few milligrams to ~200 g/ton of food/beverage The density, particle size, and geometry of the premix particles should match as closely as possible those of the feed in which the premix will be incorporated to facilitate uniform mixing. Issues such as instability, electrostatic charge, and hygroscopicity must also be addressed. The excipients present in premix formulations include carriers, liquid binders, diluents, anti-caking agents, and anti-dust agents. Carriers, such as wheat middlings, soybean mill run, and rice hulls, bind active ingredients to their surfaces and are important in attaining uniform mixing of the active ingredient. A liquid binding agent, such as a vegetable oil, should be included in the formulation whenever a carrier is used. Diluents increase the bulk of premix formulations, but unlike carriers, do not bind the active ingredients. Examples of diluents include ground limestone, dicalcium phosphate, dextrose, and kaolin. Caking in a premix formulation may be caused by hygroscopic ingredients and is addressed by adding small amounts of anti-caking agents such as calcium silicate, silicon dioxide, and hydrophobic starch. The dust associated with powdered premix formulations can have serious implications for both operator safety and economic losses, and is reduced by including a vegetable oil or light mineral oil in the formulation. An alternate approach to overcoming dust is to granulate the premix formulation.

A medicated block is a compressed feed material that contains an active ingredient, such as a drug, anthelmintic, surfactant (for bloat prevention), or a nutritional supplement, and is commonly packaged in a cardboard box. Ruminants typically have free access to the medicated block over several days, and variable consumption may be problematic. This concern is addressed by ensuring the active ingredient is nontoxic, stable, palatable, and preferably of low solubility. In addition, excipients in the formulation modulate consumption by altering the palatability and/or the hardness of the medicated block. For example, molasses increases palatability and sodium chloride decreases it. Additionally, the incorporation of a binder such as lignin sulfonate in blocks manufactured by compression or magnesium oxide in blocks manufactured by chemical reaction, increases hardness. The hygroscopic nature of molasses in a formulation may also impact the hardness of medicated blocks and is addressed by using appropriate packaging.

In another embodiment, the composition of the present invention is in a chewable oral dosage form. In another embodiment, the chewable oral dosage form is a chewable tablet. In another embodiment, the chewable tablet of the invention is taken slowly by chewing or sucking in the mouth. In another embodiment, the chewable tablet of the invention enables the vitamins contained therein to be orally administered without drinking.

In another embodiment of the present invention, the composition further comprises fructose, sorbitol, microcrystalline cellulose, magnesium stearate, or any combination thereof. In another embodiment, the composition further comprises chamomile. In another embodiment, the composition further comprises ginger. In another embodiment, the composition further comprises peppermint. In another embodiment, the composition further comprises anise. In another embodiment, the composition of the present invention is in the form of a chewing gum product. In another embodiment, chewing gum compositions contemplated by the present invention comprise all types of sugar and sugarless chewing gums and chewing gum formulations known to those skilled in the art, including regular and bubble gum types. In another embodiment, chewing gum compositions of the invention comprise a chewing gum base, a modifier, a bulking agent or sweetener, and one or more other additives such as, flavoring agents, colorants and antioxidants. In another embodiment, the modifying agents are used to soften, plasticize and/or compatibilize one or more of the components of the gum base and/or of the formulation as a whole.

In another embodiment, the present invention provides a soft, chewable dosage form which is pliable and chewy, yet dissolves quickly in the mouth, has a long shelf life, contains little moisture which improves stability and decreases the tendency for the dosage form to dry out, does not require cooking or heating as part of the manufacturing process. In another embodiment, the dosage form is used as a matrix for vitamins.

In another embodiment, the chewable tablet of the invention comprises a metal salt such as calcium, magnesium, aluminum salt, or any mixture thereof. In another embodiment, the chewable tablet of the invention comprises hydroxyalkyl cellulose. In another embodiment, the chewable tablet of the invention comprises low viscosity hydroxyalkyl cellulose. In another embodiment, the chewable tablet of the invention comprises high viscosity hydroxyalkyl cellulose.

In another embodiment, the chewable tablet of the invention comprises various additives. In another embodiment, the chewable tablet of the invention comprises sweeteners. In another embodiment, the chewable tablet of the invention comprises acidic ingredients. In another embodiment, the chewable tablet of the invention comprises taste correctives. In another embodiment, the chewable tablet of the invention comprises polymeric compounds. In another embodiment, the chewable tablet of the invention comprises essential oils.

In another embodiment, the chewable tablet of the invention is a soft tablet. In another embodiment, the chewable tablet of the invention is made in a state of soft candy. In another embodiment, the chewable tablet of the invention is made in a state of jelly.

In another embodiment, the chewable tablet of the invention comprises a core comprising the vitamins of the invention. In another embodiment, the chewable tablet of the invention comprises an outer layer wrapping the core which is made up of chewable base such as a gum, a soft candy or a caramel.

In another embodiment, sugar used in the present invention may be selected from the group consisting of white sugar, liquid glucose, sorbitol, dextrose, isomalt, liquid maltitol, aspartame and lactose, and this sugar may comprise 30-90 weight % by total weight of the ingredients.

In another embodiment, the chewable tablet of the invention comprises a sweetener such as but not limited to: glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as sucralose; sugar alcohols such as sorbitol, mannitol, xylitol, and the like. In another embodiment, glycerin, lecithin, hydrogenated palm oil or glyceryl monostearate are used as a protecting agent of crystallization of the sugars in 0.02-3.0 weight % by total weight of the ingredients, to prevent adhesion to oral cavity and improve the soft property of the products.

In another embodiment, isomalt or liquid maltitol are used as an enhancing agent of chewing property. In another embodiment, gelatin or arabic gum are used as a keeping agent of hardness and extension property in 0.1-3.0 weight % by total weight of the ingredients. In another embodiment, food flavor or a fruits extract; a souring agent such as citric acid are added in adequate amount. In another embodiment, a coloring agent such as a food color is optionally added in a small amount.

Yet a further embodiment of the present invention includes the use of an effervescent disintegration agent. In another embodiment, its action aids in the masking of objectionable taste of the vitamins.

In another embodiment, of the present invention the effervescent disintegration agent is an acid. In another embodiment, of the present invention the effervescent disintegration agent is citric acid. In another embodiment, of the present invention the effervescent disintegration agent is tartaric acid.

In another embodiment, the chewable tablet of the invention comprises a crystallization modifier such but not limited to, surfactants (Spans™ and Tweens™), dextrose, polyethylene glycol (PEG), polypropylene glycol (PPG), etc. These modifiers generally provide controlled acceleration of crystallization while the matrix is bound. In another embodiment, these crystallization modifiers enhance the formation of a crystalline frame and the conversion of the remaining mass.

In another embodiment, crystallization modifiers are surfactants having a hydrophilic to lipid balance (HLB) of six or greater, i.e., they have the same degree of hydrophilicity as surfactants characterized by degree of HLB. In another embodiment, such materials include, but are not limited to anionic, cationic and zwitterionic surfactants as well as neutral materials which have an HLB of six or greater. In another embodiment, crystallization modifiers are hydrophilic materials having polyethylene oxide linkages. In another embodiment, crystallization modifiers have a molecular weight of at least 100.

In another embodiment, the chewable tablet of the invention comprises a filler. In another embodiment, filler increases the bulk of the tablet. In another embodiment, the filler is calcium sulfate, both di- and tri basic, starch, calcium carbonate, microcrystalline cellulose, modified starches, lactose, sucrose, mannitol, sorbitol, or any combination thereof. In another embodiment, the chewable tablet of the invention comprises a binder such as but not limited to: starches, pregelatinize starches, gelatin, polyvinylpyrrolidone, methylcellulose, sodium carboxymethylcellulose, ethylcellulose, polyacrylamides, polyvinyloxoazolidone, and polyvinylalcohols.

In another embodiment, the chewable tablet of the invention comprises a lubricant such as but not limited to: magnesium stearate, calcium stearate, zinc stearate, hydrogenated vegetable oils, sterotex, polyoxyethylene, monostearate, talc, polyethyleneglycol, sodium benzoate, sodium lauryl sulfate, magnesium lauryl sulfate and light mineral oil.

In another embodiment, the chewable tablet of the invention comprises a dispersion enhancer such as but not limited to: starch, alginic acid, polyvinylpyrrolidones, guar gum, partially hydrolyzed guar gum, kaolin, bentonite, purified wood cellulose, sodium starch glycolate, isoamorphous silicate, and microcrystalline cellulose as high HLB emulsifier surfactants.

In another embodiment, the chewable tablet of the invention comprises an absorbent such as but not limited to: maltodextrin. In another embodiment, the chewable tablet of the invention comprises an emulsifier such as but not limited to: Mono- and diglycerides, Oleaginous substances such as food oils like Medium, Chain Triglycerides (MCT), and Stearine D 17.

In another embodiment, the chewable tablet of the invention comprises a water soluble bulking agent such as but not limited to: hydrocolloid thickeners and binders, such as gum arabic, pectins, modified starches, alginates, carrageenans, xanthan gums, carboxymethylcellulose, methylcellulose, hydroxyethylcellulose, hydroxypropylcellulose, hydroxypropylmethylcellulose, propylene glycol alginate, polyvinylpyrrolidone (PVP), carboxyvinyl polymers (such as Carbopol®), polyethylene oxide polymers (such as Polyox®), sorbitol, xylitol, sucrose, fructose, dextrose, mannitol, starch maltodextrin, corn syrup solids, or combinations thereof.

In another embodiment, the chewable tablet of the invention comprises a water insoluble bulking agent such as but not limited to: talc, dicalcium phosphate, powdered celluloses, microcrystalline celluloses and antacid compounds. In another embodiment, the chewable tablet of the invention comprises vitamins in compressed particles. In another embodiment, individual particles are coated with a blend of cellulose acetate or cellulose acetate butyrate and polyvinyl pyrrolidone (USP Povidone or "PVP"). In another embodiment, the coating provides excellent taste masking while still permitting acceptable bioavailability of the vitamins. In another embodiment, the chewable tablet In another embodiment, the invention relates to a composition of the invention comprised within chewable and edible soft gelatin capsules, the shells of which comprise gelatin, water, plasticizer and a hydrogenated starch hydrolysate. In another embodiment, soft gelatin shell comprises about 10-45% gelatin; about 5-30% water; about 12-35% plasticizer; and about 2-25% of a hydrogenated starch hydrolysate. In another embodiment, the shell encloses a soft gelatin capsule fill material. In another embodiment, the gelatin may be of Type A, Type B, or a mixture thereof. In another embodiment, in order to augment the taste and chewability of the capsule shell, as well as to assist in the rapid dissolution of the shell upon chewing, the present capsule shell further comprises a hydrogenated starch hydrolysate.

The compositions and dosage forms of the present invention are useful in promoting health and preventing or treating a large number of disorders in human patients and other mammalian subjects.

In additional embodiments of the present invention, compositions and methods are provided for treating and/or preventing heart disease, such as, but not limited to, atherosclerotic and hypertensive diseases, congenital heart disease, rheumatic heart disease, and other conditions.

In further embodiments of the present invention, compositions and methods are provided for treating and/or preventing peripheral blood vessel disorders. Peripheral blood vessel disorders affect the blood vessels of the arms, legs, and trunk (except those supplying the heart). These disorders include disorders of the blood vessels supplying the brain, namely cerebrovascular disorders.

In additional embodiments of the present invention, compositions and methods are provided for treating and/or preventing blood disorders, disorders of nutrition or metabolism, hormonal disorders, bone, joint or muscle disorders, spinal cord or nervous disorders, immunological disorders, infectious disorders, urinary tract and kidney disorders, or skin disorders, vitamin deficiencies and other nutritional disorders, lung or airway disorders, digestive disorders, or reproductive disorders.

The compositions may be provided to the subject in an oral dosage form. In some cases, the oral dosage form includes a capsule.

In other embodiments, the oral dosage form may be chewable. The oral dosage form may further comprise at least one of fructose, sorbitol, microcrystalline cellulose, magnesium stearate, or a combination thereof.

In some cases, the oral dosage form includes at least one additional antioxidant. The oral dosage form may also include additional agents and components.

The compositions of the present invention may comprise an additional active agent. The additional active agent is selected from the group consisting of active herbal extracts, acaricides, age spot and keratose removing agents, allergen, analgesics, local anesthetics, antiacne agents, antiallergic agents, antiaging agents, antibacterials, antibiotic agents, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, anti-wrinkle agents, antipruritics, antipsoriatic agents, antirosacea agents antiseborrheic agents, antiseptic, antiswelling agents, antiviral agents, anti-yeast agents, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, non-steroidal anti-inflammatory agents, oxidizing agents, pediculicides, photodynamic therapy agents, retinoids, sanatives, scabicides, self tanning agents, skin whitening agents, asoconstrictors, vasodilators, vitamins, vitamin D derivatives, wound healing agents and wart removers.

According to some embodiments the antibiotic agent is selected from the group consisting of beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, antibiotic steroids, sulfonamides, tetracycline, dicarboxylic acids, antibiotic metals including antibiotic metal ions, oxidizing agents, substances that release free radicals and/or active oxygen, cationic antimicrobial agents, quaternary ammonium compounds, biguanides, triguanides, bisbiguanides and analogs and polymers thereof, naturally occurring antibiotic compounds, including antibiotic plant oils and antibiotic plant extracts and any one of the following antibiotic compounds: chlorhexidine acetate, chlorhexidine gluconate and chlorhexidine hydrochloride, picloxydine, alexidine, polihexanide, chlorproguanil hydrochloride, proguanil hydrochloride, metformin hydrochloride, phenformin, buformin hydrochloride, abomycin, acetomycin, acetoxycycloheximide, acetylnanaomycin, an actinoplanes sp. compound, actinopyrone, aflastatin, albacarcin, albacarcin, albofungin, albofungin, alisamycin, alpha-R,S-methoxycarbonylbenzylmonate, altromycin, amicetin, amycin, amycin demanoyl compound, amycine, amycomycin, anandimycin, anisomycin, anthramycin, anti-syphilis imune substance, anti-tuberculosis imune substance, antibiotic from *Eschericia coli*, antibiotics from *Streptomyces* refuineus, anticapsin, antimycin, aplasmomycin, aranorosin, aranorosinol, arugomycin, ascofuranone, ascomycin, ascosin, *Aspergillus flavus* antibiotic, asukamycin, aurantinin, an Aureolic acid antibiotic substance, aurodox, avilamycin, azidamfenicol, azidimycin, bacillaene, a *Bacillus larvae* antibiotic, bactobolin, benanomycin, benzanthrin, benzylmonate, bicozamycin, bravomicin, brodimoprim, butalactin, calcimycin, calvatic acid, candiplanecin, carumonam, carzinophilin, celesticetin, cepacin, cerulenin, cervinomycin, chartreusin, chloramphenicol, chloramphenicol palmitate, chloramphenicol succinate sodium, chlorflavonin, chlorobiocin, chlorocarcin, chromomycin, ciclopirox, ciclopirox olamine, citreamicin, cladosporin, clazamycin, clecarmycin, clindamycin, coliformin, collinomycin, copiamycin, corallopyronin, corynecandin, coumermycin, culpin, cuprimyxin, cyclamidomycin, cycloheximide, dactylomycin, danomycin, danubomycin, delaminomycin, demethoxyrapamycin, demethylscytophycin, dermadin, desdamethine, dexylosylbenanomycin, pseudoaglycone, dihydromocimycin, dihydronancimycin, diumycin, dnacin, dorrigocin, dynemycin, dynemycin triacetate, ecteinascidin, efrotomycin, endomycin, ensanchomycin, equisetin, ericamycin, esperamicin, ethylmonate, everninomicin, feldamycin, flambamycin, flavensomycin, florfenicol, fluvomycin, fosfomycin, fosfonochlorin, fredericamycin, frenolicin, fumagillin, fumifungin, funginon, fusacandin, fusafungin, gelbecidine, glidobactin, grahamimycin, granaticin, griseofulvin, griseoviridin, grisonomycin, hayumicin, hayumicin, hazymicin, hedamycin, heneicomycin, heptelicid acid, holomycin, humidin, isohematinic acid, karnatakin, kazusamycin, kristenin, L-dihydrophenylalanine, a L-isoleucyl-L-2-amino-4-(4'-amino-2', 5'-cyclohexadienyl) derivative, lanomycin, leinamycin, leptomycin, libanomycin, lincomycin, lomofungin, lysolipin, magnesidin, manumycin, melanomycin, methoxycarbonylmethylmonate, methoxycarbonylethylmonate, methoxycarbonylphenylmonate, methyl pseudomonate, methylmonate, microcin, mitomalcin, mocimycin, moenomycin, monoacetyl cladosporin, monomethyl cladosporin, mupirocin, mupirocin calcium, mycobacidin, myriocin, myxopyronin, pseudoaglycone, nanaomycin, nancimycin, nargenicin, neocarcinostatin, neoenactin, neothramycin, nifurtoinol, nocardicin, nogalamycin, novobiocin, octylmonate, olivomycin, orthosomycin, oudemansin, oxirapentyn, oxoglaucine methiodide, pactacin, pactamycin, papulacandin, paulomycin, phaeoramularia fungicide, phenelfamycin, phenyl, cerulenin, phenylmonate, pholipomycin, pirlimycin, pleuromutilin, a polylactone derivative, polynitroxin, polyoxin, porfiromycin, pradimicin, prenomycin, Prop-2-enylmonate, protomycin, *Pseudomonas* antibiotic, pseudomonic acid, purpuromycin, pyrinodemin, pyrrolnitrin, pyrrolomycin, amino, chloro pentenedioic acid, rapamycin, rebeccamycin, resistomycin, reuterin, reveromycin, rhizocticin, roridin, rubiflavin, naphthyridinomycin, saframycin, saphenamycin, sarkomycin, sarkomycin, sclopularin, selenomycin, siccanin, spartanamicin, spectinomycin, spongistatin, stravidin, streptolydigin, *streptomyces arenae* antibiotic complex, streptonigrin, streptothricins, streptovitacin, streptozotocine, a strobilurin derivative, stubomycin, sulfamethoxazol-trimethoprim, sakamycin, tejeramycin, terpentecin, tetrocarcin, thermorubin, thermozymocidin, thiamphenicol, thioaurin, thiolutin, thiomarinol, thiomarinol, tirandamycin, tolytoxin, trichodermin, trienomycin, trimethoprim, trioxacarcin, tyrissamycin, umbrinomycin, unphenelfamycin, urauchimycin, usnic acid, uredolysin, variotin, vermisporin, verrucarin, metronidazole, erythromycin and analogs, salts and derivatives thereof.

According to some embodiments, the additional active agent is selected from the group consisting of alclometasone dipropionate, amcinafel, amcinafide, amcinonide, beclomethasone, beclomethasone dipropionate, betamethsone, betamethasone benzoate, betamethasone dexamethasone-phosphate, dipropionate, betamethasone valerate, budesonide, chloroprednisone, chlorprednisone acetate, clescinolone, clobetasol, clobetasol propionate, clobetasol valerate, clobetasone, clobetasone butyrate, clocortelone, cortisone, cortodoxone, craposone butyrate, desonide, desoxymethasone, dexamethasone, desoxycorticosterone acetate, dichlorisone, diflorasone diacetate, diflucortolone valerate, diflurosone diacetate, diflurprednate, fluadrenolone, flucetonide, flucloronide, fluclorolone acetonide, flucortine butylesters, fludroxycortide, fludrocortisone, flumethasone, flumethasone pivalate, flumethasone pivalate, flunisolide, fluocinolone, fluocinolone acetonide, fluocinonide, fluocortin butyl, fluocortolone, fluorometholone, fluosinolone acetonide, fluperolone, fluprednidene acetate, fluprednisolone hydrocortamate, fluradrenolone, fluradrenolone acetonide, flurandrenolone, fluticasone, halcinonide, halobetasol, hydrocortisone, hydrocortisone acetate, hydrocortisone butyrate, hydrocortisone cyclopentylpropionate, hydrocortisone valerate, hydroxyltriamcinolone, medrysone, meprednisone, .alpha.-methyl dexamethasone, methylprednisolone, methylprednisolone acetate, mometasone furoate, paramethasone, prednisolone, prednisone, pregnenolone, progesterone, spironolactone, triamcinolone, triamcinolone acetonide and derivatives, esters and salts thereof.

According to some embodiments, the compositions of the present invention comprise a metal salt such as calcium, magnesium, zinc, selenium, copper, vanadium, chromium, iron, aluminum salt, or any mixture thereof.

According to some embodiments, the compositions of the present invention further comprise a buffering agent. The buffering agent can be any of the known buffering systems used in pharmaceutical or cosmetic formulations as would be appreciated by a man of the art. It can also be an organic acid, a carboxylic acid, a fatty acid an amino acid, an aromatic acid, an alpha or beta hydroxyl acid an organic base or a nitrogen containing compound.

According to some embodiments, the compositions of the present invention further comprise a pH modulating agent. The term pH modulating agent is used to describe an agent which can effect pH in an aqueous solution the term modulating agent more particularly means an acid or base or buffer system or combinations thereof, which is introduced into or is present in and acts to modulate the ionic or polar characteristics and any acidity or basicity balance of a composition.

According to some embodiments, the compositions of the present invention further comprise an antiviral agent Suitable antiviral agents include but are not limited to, acyclovir, gancyclovir, ribavirin, amantadine, rimantadine nucleoside-analog reverse transcriptase inhibitors, such as zidovudine, didanosine, zalcitabine, tavudine, lamivudine and vidarabine, non-nucleoside reverse transcriptase inhibitors, such as nevirapine and delavirdine, protease inhibitors, such as saquinavir, ritonavir, indinavir and nelfinavir, and interferons and derivatives, esters, salts and mixtures thereof.

According to some embodiments, the compositions of the present invention further comprise a chemotherapeutic agent. Suitable chemotherapeutic agents include but are not limited to daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A, XR9576 and derivatives, esters, salts and mixtures thereof.

According to some embodiments, the compositions of the present invention further comprise a corticosteroid. Suitable corticosteroids include but are not limited to alclometasone dipropionate, amcinafel, amcinafide, amcinonide, beclomethasone, beclomethasone dipropionate, betamethsone, betamethasone benzoate, betamethasone dexamethasone-phosphate, dipropionate, betamethasone valerate, budesonide, chloroprednisone, chlorprednisone acetate, clescinolone, clobetasol, clobetasol propionate, clobetasol valerate, clobetasone, clobetasone butyrate, clocortelone, cortisone, cortodoxone, craposone butyrate, desonide, desoxymethasone, dexamethasone, desoxycorticosterone acetate, dichlorisone, diflorasone diacetate, diflucortolone valerate, diflurosone diacetate, diflurprednate, fluadrenolone, flucetonide, flucloronide, fluclorolone acetonide, flucortine butylesters, fludroxycortide, fludrocortisone, flumethasone, flumethasone pivalate, flumethasone pivalate, flunisolide, fluocinolone, fluocinolone acetonide, fluocinonide, fluocortin butyl, fluocortolone, fluorometholone, fluosinolone acetonide, fluperolone, fluprednidene acetate, fluprednisolone hydrocortamate, fluradrenolone, fluradrenolone acetonide, flurandrenolone, fluticasone, halcinonide, halobetasol, hydrocortisone, hydrocortisone acetate, hydrocortisone butyrate, hydrocortisone cyclopentylpropionate, hydrocortisone valerate, hydroxyltriamcinolone, medrysone, meprednisone, .alpha.-methyl dexamethasone, methylprednisolone, methylprednisolone acetate, mometasone furoate, paramethasone, prednisolone, prednisone, pregnenolone, progesterone, spironolactone, triamcinolone, triamcinolone acetonide and derivatives, esters, salts and mixtures thereof.

According to some embodiments, the compositions of the present invention further comprise an analgesic. Suitable analgesics include but are not limited to benzocaine, butamben picrate, dibucaine, dimethisoquin, dyclonine, lidocaine, pramoxine, tetracaine, salicylates and derivatives, esters, salts and mixtures thereof.

According to some embodiments, the compositions of the present invention further comprise a non-steroidal anti-inflammatory agent. Suitable non-steroidal anti-inflammatory agent include but are not limited to azelaic acid, oxicams, piroxicam, isoxicam, tenoxicam, sudoxicam, CP-14,304, salicylates, aspirin, disalcid, benorylate, trilisate, safapryn, solprin, diflunisal, fendosal, acetic acid derivatives, diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac, fenamates, mefenamic, meclofenamic, flufenamic, niflumic, tolfenamic acids, propionic acid derivatives, ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofen, pyrazoles, phenylbutazone, oxyphenbutazone, feprazone, azapropazone, trimethazone and derivatives, esters, salts and mixtures thereof.

According to some embodiments, the compositions of the present invention further comprise a vasodilator. Suitable vasodilators include but are not limited to agents that modulate the activity of the enzyme nitric oxide synthase, nicotinic acid, ethyl nicotinate, amyl nitrite, amyl nitrate, ethyl nitrite, butyl nitrite, isobutyl nitrite, glyceryl trinitrate, octyl nitrite, sodium nitrite, sodium nitroprusside, clonitrate, erythrityl tetranitrate, isosorbide mononitrate, isosorbide dinitrate, mannitol hexanitrate, pentaerythritol tetranitrate, penetrinitol, triethanolamine trinitrate, trolnitrate phosphate (triethanolamine trinitrate diphosphate), propatylnitrate, nitrite esters of sugars, nitrite esters of polyols, nitrate esters of sugars, nitrate esters of polyols, nicorandil, apresoline, diazoxide, hydralazine, hydrochlorothiazide, minoxidil, pentaerythritol, tolazoline, scoparone, a beta-adrenergic blocker, an alpha-adrenoceptor blocker, a prostaglandin, sildenafil, dipyridamole, catecholamine, isoproternol, furosemide, prostaglandin, prostacyclin, enalaprilat, morphine, acepromazine, prazosin ($\alpha$-blocker), enalapril, Captopril, amlodipine, minoxidil, tadalafil, vardenafil, phenylephrin, etilefein, caffeine, capsaicin, an extract capsicum, achillea millefolium (Yarrow), allium sativum (garlic), amoracia rusticana (horseradish), berberis vulgaris (barberry), cimicifuga racemosa (black cohosh), coleus forskholii (coleus), coptis (goldenthread), crataegus (hawthorn), eleutherococcus senticosus (siberian ginseng), ginkgo biloba(ginkgo), melissa offiicnalis (lemon balm), olea europaea (olive leaf), panax ginseng (Chinese ginseng), petroselinum crispum (parsley), scutellaria baicalensis (baical skullcap), tilia europaea (linden flower), trigonella foenum-graecum (fenugreek), urtica dioica (nettles), valeriana officinalis (valerian), viburnum (cramp, bark, black haw), veratrum viride (American hellebore), verbena officinalis (vervain), xanthoxylum americanum (prickly ash), zingiber officinale (ginger), rauwolfia serpentina (Indian snakeroot), viscum album, wild yam, sasparilla, licorice, damiana, yucca, saw palmetto, gotu kola (centella asiatica), yohimbine and salts, hazel nut, brazil nut and walnut, and derivatives, esters, salts and mixtures thereof.

According to some embodiments, the compositions of the present invention further comprise a vasoconstrictor. Suitable vasodilators include but are not limited to ephedrine, epinephrine, phenylephrine, angiotensin, vasopressin; an extract ephedra sinica (ma huang), polygonum bistorta (bistort root), hamamelis virginiana (witch hazel), hydrastis canadensis (goldenseal), lycopus virginicus (bugleweed), aspidosperma quebracho (quebracho blanco), cytisus scoparius (scotch broom) and cypressand and derivatives, esters, salts and mixtures thereof.

Vitamin C

Vitamin C may be produced according to any method known in the art today or by any future method. The vitamin C may be from a natural source, semi-synthetic source, synthetic source or combinations thereof. It may be extracted from one or more animal or vegetable sources, produced by fermentation, chemically synthesized or modified, or any combination of the aforesaid.

In another embodiment, vitamin C comprises the L-enantiomer of ascorbate.

According to some embodiments, vitamin C is provided as calcium ascorbate, which is non-acidic (pH neutral), making it gentle on the digestive system.

EXAMPLES

Example 1

A 30 year old male (70 kg) suffering from EVD (Ebola virus disease) has had a fever for three days. A blood test is positive for Ebola and he has a virus count of $10^5$ PFU/ml (putting him into a fatality risk group).

He is provided with the following non-drug cocktail:

| PRODUCT | FUNCTION | QUANTITY | ED XX (LITERATURE, ASSUMED OR ESTIMATED) | |
|---|---|---|---|---|
| INITIAL LOAD PFU/ML | | | | 100000 pfu/ml |
| VITAMIN C | TNF ALPHA INHIBITOR NKAPPAB PATHWAY INHIBITOR ANTIVIRAL COLLAGEN PRECURSOR | 2 g/day | 50 | 50000 pfu/ml |
| CURCUMIN (bioavailable) The Indians consume up to 8 g/day. | TNF ALPHA INHIBITOR NKAPPAB PATHWAY INHIBITOR ANTIVIRAL Blocker of sepsis-induced muscle proteolysis | 2 g/day | 50 | 25000 pfu/ml |

-continued

| PRODUCT | FUNCTION | QUANTITY | ED XX (LITERATURE, ASSUMED OR ESTIMATED) | |
|---|---|---|---|---|
| BETA-URSOLIC ACID (naturally occurring in onion/garlic) | (CAT B) CATHEPSIN B INHIBITOR | 0.2 g/day | 50 | 12500 pfu/ml |
| BETA-OLEANOLIC ACID (naturally occurring in onion/garlic) | (CAT B) CATHEPSIN B INHIBITOR | 0.04 g/day | 85 | 1875 pfu/ml |
| QUERCETIN | (CAT B) CATHEPSIN B INHIBITOR | 0.06 g/day | 75 | 469 pfu/ml |
| BERBERINE | (CAT B) CATHEPSIN B INHIBITOR | 0.185 g/day | 50 | 235 pfu/ml |
| VANADATE | (CAT B) CATHEPSIN B INHIBITOR | 1.5 mg/day | 10 | 212 pfu/ml |
| EGCG (epigallocatechin-3 gallate) | Folate remover NKAPPAB PATHWAY INHIBITOR | 1 g/day | 50 | 106 pfu/ml |
| Total Estimated viral load reduction factor $N_0$/Nt | | | | Around 1000 fold reduction |

In fact, such a combination may prove even better, since, for example curcumin and EGCG are known to act synergistically in other models (Khafif et al., 1998) and these compounds are active in several metabolic pathways. Thus, this kind of therapy could move this person from the fatality risk group into the survivors' group.

In some cases, it would be good, where possible, to provide this combination together with sodium, potassium, magnesium ions by drip infusion. Additionally, vitamin B1 (thiamine), calcium, copper, zinc, selenium and iron ions to the infusion should improve the patient's metabolism.

Example 2

A three-month old female baby (5 kg) suffering from EVD (Ebola virus disease) has had a fever for four days and is listless. A blood test is positive for Ebola and she has a virus count of $10^7$ PFU/ml (putting her into a fatality risk group).

She is provided with the following cocktail:

| PRODUCT | FUNCTION | QUANTITY | ED XX (ASSUMED OR ESTIMATED) | Residual estimated viral load |
|---|---|---|---|---|
| INITIAL LOAD PFU/ML | | | | $10^7$ pfu/ml |
| 3-DEAZANEPLANOCIN A | (SAHH) INHIBITOR | 5 mg | | $10^5$ pfu/ml |
| VITAMIN C | TNF ALPHA INHIBITOR NKAPPAB | 0.15 g/day | 50 | 50000 pfu/ml |

-continued

| PRODUCT | FUNCTION | QUANTITY | ED XX (ASSUMED OR ESTIMATED) | Residual estimated viral load |
|---|---|---|---|---|
| | PATHWAY INHIBITOR ANTIVIRAL COLLAGEN PRECURSOR | | | |
| CURCUMIN (bioavailable) The Indians consume up to 8 g/day. | TNF ALPHA INHIBITOR NKAPPAB PATHWAY INHIBITOR ANTIVIRAL Blocker of sepsis-induced muscle proteolysis | 0.1 g/day | 50 | 25000 pfu/ml |
| BETA-URSOLIC ACID (naturally occurring in onion/garlic) | (CAT B) CATHEPSIN B INHIBITOR | 0.2 g/day | 50 | 12500 pfu/ml |
| BETA-OLEANOLIC ACID (naturally occurring in onion/garlic) | (CAT B) CATHEPSIN B INHIBITOR | 0.004 g/day | 85 | 1875 pfu/ml |
| QUERCETIN | (CAT B) CATHEPSIN B INHIBITOR | 0.006 g/day | 75 | 469 pfu/ml |
| BERBERINE | (CAT B) CATHEPSIN B INHIBITOR | 0.0185 g/day | 50 | 235 pfu/ml |
| VANADATE | (CAT B) CATHEPSIN B INHIBITOR | 0.15 mg/day | 10 | 212 pfu/ml |
| EGCG (epigallocatechin-3 gallate) | Folate remover NKAPPAB PATHWAY INHIBITOR | 0.1 g/day | 50 | 106 pfu/ml |
| Estimated viral load reduction factor N0/Nt | | | | Around 100,000 fold reduction |

In fact, such a combination may prove even better, since, for example curcumin and EGCG are known to act synergistically in other models (Khafif et al., 1998) and these compounds are active in several metabolic pathways. Thus, this kind of therapy could move this person from the fatality risk group into the survivors' group.

Example 3

A 30 year old male (70 kg) suffering from EVD (Ebola virus disease) has had a fever for five days. A blood test is positive for Ebola and he has a virus count of $10^9$ PFU/ml (putting him into a fatality risk group).

He is provided with the following cocktail:

| PRODUCT | FUNCTION | QUANTITY | ED XX (ASSUMED OR ESTIMATED) | Residual estimated viral load |
|---|---|---|---|---|
| INITIAL LOAD PFU/ML | | | | $10^9$ pfu/ml |
| 3-DEAZANEPLANOCIN A | (SAHH) INHIBITOR | 70 mg | | $10^7$ pfu/ml |
| Arginine | COLLAGEN PRECURSOR | 2.5 g/day | | $10^7$ pfu/ml |
| Ornithine | COLLAGEN PRECURSO | 3.5 g/day | | $10^7$ pfu/ml |
| VITAMIN C | TNF ALPHA INHIBITOR NKAPPAB PATHWAY INHIBITOR ANTIVIRAL COLLAGEN PRECURSOR | 4 g/day | 50 | 500000 pfu/ml |
| CURCUMIN (bioavailable) The Indians consume up to 8 g/day. | TNF ALPHA INHIBITOR NKAPPAB PATHWAY INHIBITOR ANTIVIRAL Blocker of sepsis-induced muscle proteolysis | 2 g/day | 25 | 37500 pfu/ml |
| BETA-URSOLIC ACID (naturally occurring in onion/garlic) | (CAT B) CATHEPSIN B INHIBITOR | 0.4 g/day | 50 | 12500 pfu/ml |
| BETA-OLEANOLIC ACID (naturally occurring in onion/garlic) | (CAT B) CATHEPSIN B INHIBITOR | 0.01 g/day | 50 | 6250 pfu/ml |
| QUERCETIN | (CAT B) CATHEPSIN B INHIBITOR | 0.06 g/day | 50 | 3125 pfu/ml |
| BERBERINE | (CAT B) CATHEPSIN B INHIBITOR | 0.185 g/day | 75 | 2344 pfu/ml |
| VANADATE | (CAT B) CATHEPSIN B INHIBITOR | 0.15 mg/day | 10 | 2109 pfu/ml |
| EGCG (epigallocatechin-3 gallate) | Folate remover NKAPPAB PATHWAY INHIBITOR | 1 g/day | 75 | 1582 pfu/ml |
| adenosine | -ADENOSYL HOMO-CYSTEINE HYDROLASE (SAHH) INHIBITOR ENDOTHELIAL BARRIER ENHANCER | 4 g/day | 75 | 1186 |
| Estimated viral load reduction factor N0/Nt | | | | Around 843,000 fold reduction |

Example 4

A 30 year old male (70 kg) suffering from EVD (Ebola virus disease) has had a fever for seven days and has profuse internal bleeding and skin lesions. A blood test is positive for Ebola and he has a virus count of $10^{10}$ PFU/ml (putting him into a fatality risk group).

He is provided with the following cocktail:

| PRODUCT | FUNCTION | QUANTITY | ED XX (ASSUMED OR ESTIMATED) | Residual estimated viral load |
|---|---|---|---|---|
| INITIAL LOAD PFU/ML | | | | $10^{10}$ pfu/ml |
| 3-DEAZANEPLANOCIN A | (SAHH) INHIBITOR | 70 mg | | $10^{8}$ pfu/ml |
| MIGLUSTAT | α-glucosidase inhibitor | 2 g/day | | $10^{7}$ pfu/ml |
| Arginine | COLLAGEN PRECURSOR | 2.5 g/day | | $10^{7}$ pfu/ml |
| Ornithine | COLLAGEN PRECURSO | 3.5 g/day | | $10^{7}$ pfu/ml |
| VITAMIN C | TNF ALPHA INHIBITOR NKAPPAB PATHWAY INHIBITOR ANTIVIRAL COLLAGEN PRECURSOR | 4 g/day | 50 | 500000 pfu/ml |
| CURCUMIN (bioavailable) The Indians consume up to 8 g/day. | TNF ALPHA INHIBITOR NKAPPAB PATHWAY INHIBITOR ANTIVIRAL Blocker of sepsis-induced muscle proteolysis | 2 g/day | 25 | 37500 pfu/ml |
| BETA-URSOLIC ACID (naturally occurring in onion/garlic) | (CAT B) CATHEPSIN B INHIBITOR | 0.4 g/day | 50 | 12500 pfu/ml |
| BETA-OLEANOLIC ACID (naturally occurring in onion/garlic) | (CAT B) CATHEPSIN B INHIBITOR | 0.01 g/day | 50 | 6250 pfu/ml |
| QUERCETIN | (CAT B) CATHEPSIN B INHIBITOR | 0.06 g/day | 50 | 3125 pfu/ml |
| BERBERINE | (CAT B) CATHEPSIN B INHIBITOR | 0.185 g/day | 75 | 2344 pfu/ml |
| VANADATE | (CAT B) CATHEPSIN B INHIBITOR | 0.15 mg/day | 10 | 2109 pfu/ml |
| EGCG (epigallocatechin-3 gallate) | Folate remover NKAPPAB PATHWAY INHIBITOR | 1 g/day | 75 | 1582 pfu/ml |
| adenosine | -ADENOSYL HOMO-CYSTEINE HYDROLASE (SAHH) INHIBITOR ENDOTHELIAL BARRIER ENHANCER | 4 g/day | 75 | 1186 |
| Estimated viral load reduction factor N0/Nt | | | | Around $8.4 \times 10^{6}$ fold reduction |

In fact, such a combination may prove even better, since, for example curcumin and EGCG are known to act synergistically in other models (Khafif et al., 1998) and these compounds are active in several metabolic pathways. Thus, this kind of therapy could move this person from the fatality risk group into the survivors' group. However, one cannot predict survival at a late stage of this disease.

Example 5

A 30 year old male (70 kg) suffering from EVD (Ebola virus disease) has had a fever for seven days and has profuse internal bleeding and skin lesions. A blood test is positive for Ebola and he has a virus count of $10^{10}$ PFU/ml (putting him into a fatality risk group).

He is provided with the following cocktail:

| PRODUCT | FUNCTION | QUANTITY | ED XX (ASSUMED OR ESTIMATED) | Residual estimated viral load |
|---|---|---|---|---|
| INITIAL LOAD PFU/ML | | | | $10^{10}$ pfu/ml |
| EGCG (epigallocatechin-3 gallate) | 1) Folate remover 2) CAT B) CATHEPSIN B INHIBITOR 3) HSPA5 ATP binding site inhibitor 4) NKAPPAB PATHWAY INHIBITOR | 0.7 g/day | 80 | $2 \times 10^{9}$ pfu/ml |
| BERBERINE | (CAT B) CATHEPSIN B INHIBITOR | 0.185 g/day | 75 | $5 \times 10^{8}$ pfu/ml |
| BETA-URSOLIC ACID (naturally occurring in onion/garlic) | (CAT B) CATHEPSIN B INHIBITOR | 0.4 g/day | 50 | $2.5 \times 10^{8}$ pfu/ml |
| BETA-OLEANOLIC ACID (naturally occurring in onion/garlic) | (CAT B) CATHEPSIN B INHIBITOR | 0.01 g/day | 50 | $1.25 \times 10^{8}$ pfu/ml |
| QUERCETIN | (CAT B) CATHEPSIN B INHIBITOR | 0.06 g/day | 50 | $6.25 \times 10^{7}$ pfu/ml |
| CURCUMIN (bioavailable) The Indians consume up to 8 g/day. | TNF ALPHA INHIBITOR NKAPPAB PATHWAY INHIBITOR ANTIVIRAL Blocker of sepsis-induced muscle proteolysis | 2 g/day | 25 | $1.56 \times 10^{7}$ pfu/ml |
| VITAMIN C | TNF ALPHA INHIBITOR NKAPPAB PATHWAY INHIBITOR ANTIVIRAL COLLAGEN PRECURSOR | 4 g/day | 50 | $7.8 \times 10^{6}$ pfu/ml |
| optional | | | | |
| Arginine | COLLAGEN PRECURSOR | 2.5 g/day | | $7.8 \times 10^{6}$ pfu/ml |
| Ornithine | COLLAGEN PRECURSO | 3.5 g/day | | $7.8 \times 10^{6}$ pfu/ml |
| adenosine | -ADENOSYL HOMO-CYSTEINE | 4 g/day | 75 | $1.9 \times 10^{6}$ pfu/ml |

-continued

| PRODUCT | FUNCTION | QUANTITY | ED XX (ASSUMED OR ESTIMATED) | Residual estimated viral load |
|---|---|---|---|---|
| | HYDROLASE (SAHH) INHIBITOR ENDOTHELIAL BARRIER ENHANCER | | | |
| Estimated viral load reduction factor N0/Nt | | | | Around 5300 fold reduction |

Example 6

A 30 year old male (70 kg) suffering from EVD (Ebola virus disease) has had a fever for seven days and has profuse internal bleeding and skin lesions. A blood test is positive for Ebola and he has a virus count of $10^{10}$ PFU/ml (putting him into a fatality risk group).

He is provided with the following cocktail:

| PRODUCT | FUNCTION | QUANTITY | ED XX (ASSUMED OR ESTIMATED) | Residual estimated viral load |
|---|---|---|---|---|
| INITIAL LOAD PFU/ML | | | | $10^{10}$ pfu/ml |
| EGCG (epigallocatechin-3 gallate) | 1) Folate remover 2) CAT B) CATHEPSIN B INHIBITOR 3) HSPA5 ATP binding site inhibitor 4) NKAPPAB PATHWAY INHIBITOR | 6 g/day | 90 (see St Patrick Reid et al., 2014) | $1 \times 10^9$ pfu/ml |
| BERBERINE | (CAT B) CATHEPSIN B INHIBITOR | 0.185 g/day | 75 | $2.5 \times 10^8$ pfu/ml |
| BETA-URSOLIC ACID (naturally occurring in onion/garlic) | (CAT B) CATHEPSIN B INHIBITOR | 0.4 g/day | 50 | $1.25 \times 10^8$ pfu/ml |
| BETA-OLEANOLIC ACID (naturally occurring in onion/garlic) | (CAT B) CATHEPSIN B INHIBITOR | 0.01 g/day | 50 | $6.25 \times 10^7$ pfu/ml |
| QUERCETIN | (CAT B) CATHEPSIN B INHIBITOR | 0.06 g/day | 50 | $3.125 \times 10^7$ pfu/ml |
| CURCUMIN (bioavailable) The Indians consume up to 8 g/day. | TNF ALPHA INHIBITOR NKAPPAB PATHWAY INHIBITOR ANTIVIRAL Blocker of sepsis-induced muscle proteolysis | 2 g/day | 25 | $7.8 \times 10^6$ pfu/ml |
| VITAMIN C | TNF ALPHA INHIBITOR NKAPPAB PATHWAY INHIBITOR ANTIVIRAL COLLAGEN PRECURSOR | 4 g/day | 50 | $3.9 \times 10^6$ pfu/ml |
| optional | | | | |
| Arginine | COLLAGEN PRECURSOR | 2.5 g/day | | $3.9 \times 10^6$ pfu/ml |
| Ornithine | COLLAGEN PRECURSO | 3.5 g/day | | $3.9 \times 10^6$ pfu/ml |
| Estimated viral load reduction factor N0/Nt | | | | Around 2600 fold reduction |

Example 7

A 30 year old male (70 kg) suffering from EVD (Ebola virus disease) has had a fever for seven days and has profuse internal bleeding and skin lesions. A blood test is positive for Ebola and he has a virus count of $10^{10}$ PFU/ml (putting him into a fatality risk group).

He is provided with the following cocktail:

| PRODUCT | FUNCTION | QUANTITY | ED XX (ASSUMED OR ESTIMATED) | Residual estimated viral load |
|---|---|---|---|---|
| INITIAL LOAD PFU/ML | | | | $10^{10}$ pfu/ml |
| EGCG (epigallocatechin-3 gallate) | 1) Folate remover 2) CAT B) CATHEPSIN B INHIBITOR 3) HSPA5 ATP binding site inhibitor 4) NKAPPAB PATHWAY INHIBITOR | 3.2 g/day | 90 (see St Patrick Reid et al., 2014) | $1 \times 10^9$ pfu/ml |
| BERBERINE | (CAT B) CATHEPSIN B INHIBITOR | 0.185 g/day | 75 | $2.5 \times 10^8$ pfu/ml |
| BETA-URSOLIC ACID (naturally occurring in onion/garlic) | (CAT B) CATHEPSIN B INHIBITOR | 0.4 g/day | 50 | $1.25 \times 10^8$ pfu/ml |
| BETA-OLEANOLIC ACID (naturally occurring in onion/garlic) | (CAT B) CATHEPSIN B INHIBITOR | 0.01 g/day | 50 | $6.25 \times 10^7$ pfu/ml |
| QUERCETIN | (CAT B) CATHEPSIN B INHIBITOR | 0.06 g/day | 50 | $3.125 \times 10^7$ pfu/ml |
| CURCUMIN (bioavailable) The Indians consume up to 8 g/day. | TNF ALPHA INHIBITOR NKAPPAB PATHWAY INHIBITOR ANTIVIRAL | 2 g/day | 25 | $7.8 \times 10^6$ pfu/ml |

-continued

| PRODUCT | FUNCTION | QUANTITY | ED XX (ASSUMED OR ESTIMATED) | Residual estimated viral load |
|---|---|---|---|---|
| VITAMIN C | Blocker of sepsis-induced muscle proteolysis TNF ALPHA INHIBITOR NKAPPAB PATHWAY INHIBITOR ANTIVIRAL COLLAGEN PRECURSOR | 4 g/day | 50 | $3.9 \times 10^6$ pfu/ml |
| optional | | | | |
| Arginine | COLLAGEN PRECURSOR | 2.5 g/day | | $3.9 \times 10^6$ pfu/ml |
| Ornithine | COLLAGEN PRECURSO | 3.5 g/day | | $3.9 \times 10^6$ pfu/ml |
| Estimated viral load reduction factor N0/Nt | | | | Around 2600 fold reduction |

Example 8

A three-month old female baby (5 kg) suffering from EVD (Ebola virus disease) has had a fever for four days and is listless. A blood test is positive for Ebola and she has a virus count of $10^7$ PFU/ml (putting her into a fatality risk group).

She is provided with the following cocktail:

| PRODUCT | FUNCTION | QUANTITY | ED XX (ASSUMED OR ESTIMATED) | Residual estimated viral load |
|---|---|---|---|---|
| INITIAL LOAD PFU/ML | | | | $10^7$ pfu/ml |
| VITAMIN C | TNF ALPHA INHIBITOR NKAPPAB PATHWAY INHIBITOR ANTIVIRAL COLLAGEN PRECURSOR | 2 g/day | 90 | $10^6$ pfu/ml |
| CURCUMIN (bioavailable) The Indians consume up to 8 g/day. | TNF ALPHA INHIBITOR NKAPPAB PATHWAY INHIBITOR ANTIVIRAL Blocker of sepsis-induced muscle proteolysis | 0.2 g/day | 75 | 250000 pfu/ml |
| BETA-URSOLIC ACID (naturally occurring in onion/garlic) | (CAT B) CATHEPSIN B INHIBITOR | 0.2 g/day | 50 | 125000 pfu/ml |
| BETA-OLEANOLIC ACID (naturally occurring in onion/garlic) | (CAT B) CATHEPSIN B INHIBITOR | 0.004 g/day | 85 | 18750 pfu/ml |

-continued

| PRODUCT | FUNCTION | QUANTITY | ED XX (ASSUMED OR ESTIMATED) | Residual estimated viral load |
|---|---|---|---|---|
| EGCG (epigallocatechin-3 gallate) | Folate remover NKAPPAB PATHWAY INHIBITOR | 0.1 g/day | 50 | 9375 pfu/ml |
| Estimated viral load reduction factor N0/Nt | | | | Around 1000 fold reduction |

Example 8 might be appropriate for use in pregnant women, too (but adjusted to the weight of the subject).

Example 9

A six-month old male baby (7 kg) suffering from EVD (Ebola virus disease) has had a fever for four days and is listless. A blood test is positive for Ebola and he has a virus count of $10^8$ PFU/ml (putting him into a fatality risk group).

He is provided with the following:

| PRODUCT | FUNCTION | QUANTITY | ED XX (ASSUMED OR ESTIMATED) | Residual estimated viral load |
|---|---|---|---|---|
| INITIAL LOAD PFU/ML | | | | $10^8$ pfu/ml |
| Oleuropein | VIRAL FUSION AND INTEGRATION Vp30 activator inhibitor | 40 mg/day | 80 | $2 \times 10^7$ |
| Hydroxytyrosol | VIRAL FUSION AND INTEGRATION | 15 mg/day | 80 | $4 \times 10^6$ |
| Mycophenolic acid | INOSINE MONO-PHOSPHATE DEHYDRO-GENASE INHIBITOR AND/OR RNA TRANSLATION | 0.7 mg/day | 50 | $2 \times 10^6$ |
| EGCG (epigallocatechin-3 gallate) | Folate remover NKAPPAB PATHWAY INHIBITOR | 0.2 g/day | 50 | $10^6$ pfu/ml |
| BETA-OLEANOLIC ACID | (CAT B) CATHEPSIN B INHIBITOR | 0.005 g/day | 85 | $1.5 \times 10^5$ |
| Estimated viral load reduction factor N0/Nt | | | | Around 666 fold reduction |

Example 10

A six-month old male baby (7 kg) suffering from EVD (Ebola virus disease) has had a fever for four days and is listless. A blood test is positive for Ebola and he has a virus count of $10^8$ PFU/ml (putting him into a fatality risk group).

He is provided with the following:

| PRODUCT | FUNCTION | QUANTITY | ED XX (ASSUMED OR ESTIMATED) | Residual estimated viral load |
|---|---|---|---|---|
| INITIAL LOAD PFU/ML | | | | $10^8$ pfu/ml |
| Oleuropein | VIRAL FUSION AND INTEGRATION Vp30 activator inhibitor | 40 mg/day | 80 | $2 \times 10^7$ |
| Hydroxytyrosol | VIRAL FUSION AND INTEGRATION | 15 mg/day | 80 | $4 \times 10^6$ |
| Mycophenolic acid | INOSINE MONO-PHOSPHATE DEHYDRO-GENASE INHIBITOR AND/OR RNA TRANSLATION | 0.7 mg/day | 50 | $2 \times 10^6$ |
| EGCG (epigallocatechin-3 gallate) | Folate remover NKAPPAB PATHWAY INHIBITOR | 0.2 g/day | 50 | $10^6$ pfu/ml |
| BETA-OLEANOLIC ACID | (CAT B) CATHEPSIN B INHIBITOR | 0.005 g/day | 85 | $1.5 \times 10^5$ |
| Estimated viral load reduction factor N0/Nt | | | | Around 666 fold reduction |

It should be understood that these tables provide "sequential reduction in the viral load". However, when all products are provided together in one composition (cocktail), then this reduction should be in parallel. Moreover, if these doses of the composition are provided repeatedly, then the fold reduction should be repeated or near to repeated.

Example 11. Analysis of In Vitro and In Vivo Neutralizing Activity of Different Compounds Against a Virus Such as Ebola Virus For in vitro neutralization studies, plaque reduction neutralization assays (PRNT80) will be performed. To this end, six ten-fold serial dilutions of a concentrated compound (or cocktail of compounds) are mixed with 100 plaque-forming units of Ebolavirus Sudan Gulu at 37° C. for 1 hour in the presence and absence of 5% guinea pig complement (Cedarlane) and used to infect Vero cell monolayers. Cells are overlaid with agarose and a second overlay containing 5% neutral red is added 8 days later. Plaques are counted the next day. Neutralization titers are determined to be the last dilution of serum that reduced the number of plaques by 80% compared with control wells. The experiments were repeated six times.

Exemplary Results

| Compound | Molarity at last dilution | CAS NO. |
|---|---|---|
| ribovirin | 25 μM | 36791-04-5 |
| CAC3ADO | 200 μM | 6736-58-9 |
| EPZ5676 | 400 nanoM | 1380288-87-8 |

It should be further noted that these cocktails may be provided in one or two mixed compositions, or some compounds may be provided separately. Additionally, according to some embodiments, the dosage regimes may be spread over 12 or over 24 hours, as is known in the art.

In cases where no concentration is provided, standard commercially available concentration/daily dosage of dosage forms of the same vitamin/antioxidant/drug are assumed. Disorders deemed to be within the scope of the present invention include endogenous viral infections, responses to vaccinations and/or immunizations, allergic responses.

The references cited herein teach many principles that are applicable to the present invention. Therefore the full contents of these publications are incorporated by reference herein where appropriate for teachings of additional or alternative details, features and/or technical background.

The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

ACKNOWLEDGEMENTS

We would like to acknowledge the Jeremy Coller Foundation, London, UK, for providing a grant for funding part of the initial research in this project. We would also like to thank Dr. Leslie Lobel for his technical assistance in this project.

REFERENCES

1. Fernandez-Garcia, Maria-Dolores, et al. "Pathogenesis of flavivirus infections: using and abusing the host cell." *Cell host & microbe* 5.4 (2009): 318-328.
2. Garamszegi, Sara, et al. "Transcriptional Correlates of Disease Outcome in Anticoagulant-Treated Non-Human Primates Infected with Ebolavirus." *PLoS neglected tropical diseases* 8.7 (2014): e3061.
3. Wahl-Jensen, Victoria M., et al. "Effects of Ebola virus glycoproteins on endothelial cell activation and barrier function." *Journal of virology* 79.16 (2005): 10442-10450.
4. Zappia, Vincenzo, Cynthia R. Zydek-Cwick, and F. Schlenk. "The specificity of S-adenosylmethionine derivatives in methyl transfer reactions." *Journal of Biological Chemistry* 244.16 (1969): 4499-4509.
5. Pugh, C. S., Ronald T. Borchardt, and H. O. Stone. "Sinefungin, a potent inhibitor of virion mRNA (guanine-7-)-methyltransferase, mRNA (nucleoside-2'-)-methyltransferase, and viral multiplication." *Journal of Biological Chemistry* 253.12 (1978): 4075-4077.
6. Boeck, L. D., et al. "A9145, a new adenine-containing antifungal antibiotic: fermentation." *Antimicrobial agents and chemotherapy* 3.1 (1973): 49-56.
7. Fukuda, Koji, et al. "Production improvement of antifungal, antitrypanosomal nucleoside sinefungin by <i>rpoB</i> mutation and optimization of resting cell system of <i>*Streptomyces incarnatus* <i> NRRL 8089." *Journal of bioscience and bioengineering* 109.5 (2010): 459-465.
8. Kusaka, Taiki, et al. "*Streptomyces citricolor* nov. sp. and a new antibiotic, aristeromycin." *The Journal of antibiotics* 21.4 (1968): 255.

9. Bray, Mike, and Siddhartha Mahanty. "Ebola hemorrhagic fever and septic shock." *Journal of Infectious Diseases* 188.11 (2003): 1613-1617.

10. Baize, S., et al. "Inflammatory responses in Ebola virus-infected patients."*Clinical & Experimental Immunology* 128.1 (2002): 163-168.

11. Geisbert, Thomas W., et al. "Pathogenesis of Ebola hemorrhagic fever in primate models: evidence that hemorrhage is not a direct effect of virus-induced cytolysis of endothelial cells." *The American journal of pathology* 163.6 (2003): 2371-2382.

12. James, S. Jill, et al. "Elevation in S-adenosylhomocysteine and DNA hypomethylation: potential epigenetic mechanism for homocysteine-related pathology." *The Journal of nutrition* 132.8 (2002): 2361S-2366S.

13. Pharmaceutical composition and method of inhibiting virus U.S. Pat. No. 5,011,829 A Inventors Martin S. Hirsch, Victoria A. Johnson 14. Hershfield, M. S. "Apparent suicide inactivation of human lymphoblast S-adenosylhomocysteine hydrolase by 2'-deoxyadenosine and adenine arabinoside. A basis for direct toxic effects of analogs of adenosine." *Journal of Biological Chemistry* 254.1 (1979): 22-25.

15. Bowie, Andrew G., and Luke A J O'Neill. "Vitamin C inhibits NF-κB activation by TNF via the activation of p38 mitogen-activated protein kinase." *The Journal of Immunology* 165.12 (2000): 7180-7188.

16. Hemilä, Harri. "Vitamin C and the common cold." *British Journal of Nutrition* 67.01 (1992): 3-16.

17. Anand, Preetha, et al. "Bioavailability of curcumin: problems and promises."*Molecular pharmaceutics* 4.6 (2007): 807-818.

18. Chang, Jinhong, et al. "Imino sugar glucosidase inhibitors as broadly active anti-filovirus agents." *Emerging Microbes & Infections* 2.11 (2013): e77.

19. Djurhuus, Rune, Asbjørn M. Svardal, and Per M. Ueland. "Differential Effects on Growth, Homocysteine, and Related Compounds of Two Inhibitors of S-Adenosylhomocysteine Catabolism, 3-Deazaadenosine, and 3-Deazaaristeromycin, in C3H/10T1/2 Cells." *Cancer research* 49.2 (1989): 324-330.

20. Wolberg, Gerald, et al. "Adenosine inhibition of lymphocyte-mediated cytolysis: possible role of cyclic adenosine monophosphate." *Science* 187.4180 (1975): 957-959.

21. Method of inhibiting virus U.S. Pat. No. 4,849,430 A Inventors George W. J. Fleet, Thomas W. Rademacher, Raymond A. Dwek 22. Iminosugar compounds with antiflavirus activity U.S. Pat. No. 8,097,728 B2 Inventors Baohua Gu, Timothy M. Block, Robert M. Moriarty, Mahendra N. Deshpande, Rajendra C. Shah, Less 23. Avila, José Luis, et al. "Sinefungin as treatment for American Leishmania in sensitive BALB/c and resistant C57BL/6 mice." *The American journal of tropical medicine and hygiene* 43.2 (1990): 139-145.

24. Radeke, Heike S., et al. "Interactions of (−)-ilimaquinone with methylation enzymes: Implications for vesicular-mediated secretion." *Chemistry & biology* 6.9 (1999): 639-647.

25. De Clercq, Erik, et al. "Broad-spectrum antiviral activities of neplanocin A, 3-deazaneplanocin A, and their 5'-nor derivatives." *Antimicrobial agents and chemotherapy* 33.8 (1989): 1291-1297.

26. Huggins, John, Zhen-Xi Zhang, and Mike Bray. "Antiviral drug therapy of filovirus infections: S-adenosylhomocysteine hydrolase inhibitors inhibit Ebola virus in vitro and in a lethal mouse model." *Journal of Infectious Diseases* 179. Supplement 1 (1999): S240-S247.

27. Ueland, P. M. "Pharmacological and biochemical aspects of S-adenosylhomocysteine and S-adenosylhomocysteine hydrolase." *Pharmacol Rev* 34.3 (1982): 223-253.

28. Daelemans, Dirk, et al. "S-adenosylhomocysteine hydrolase inhibitors interfere with the replication of human immunodeficiency virus type 1 through inhibition of the LTR transactivation." *Molecular pharmacology* 52.6 (1997): 1157-1163.

29. Strakova, Jana, et al. "Dietary intake of <i> S</i>-(<i>α</i>-carboxybutyl)-dl-homocysteine induces hyperhomocysteinemia in rats." *Nutrition Research* 30.7 (2010): 492-500.

30. De Clercq, E. R. I. K. "Antiviral and antimetabolic activities of neplanocins."*Antimicrobial agents and chemotherapy* 28.1 (1985): 84-89.

31. Perna, Akssandra F., et al. "Metabolic consequences of folate-induced reduction of hyperhomocysteinemia in uremia." *Journal of the American Society of Nephrology* 8.12 (1997): 1899-1905.

32. O'Dea, Robert F., et al. "Effect of adenosine analogues on protein carboxylmethyltransferase, S-adenosylhomocysteine hydrolase, and ribonucleotide reductase activity in murine neuroblastoma cells." *Cancer research* 47.14 (1987): 3656-3661.

33. Sadek, Ramses F., et al. "Ebola hemorrhagic fever, Democratic Republic of the Congo, 1995: determinants of survival." *Journal of Infectious Diseases* 179. Supplement 1 (1999): S24-S27.

34. Geisbert, Thomas W., et al. "Treatment of Ebola virus infection with a recombinant inhibitor of factor VIIa/tissue factor: a study in rhesus monkeys."*The Lancet* 362.9400 (2003): 1953-1958.

35. Bowie, Andrew G., and Luke A J O'Neill. "Vitamin C inhibits NF-κB activation by TNF via the activation of p38 mitogen-activated protein kinase." *The Journal of Immunology* 165.12 (2000): 7180-7188.

36. Tanaka, Keiji, Lloyd Waxman, and Alfred L. Goldberg. "Vanadate inhibits the ATP-dependent degradation of proteins in reticulocytes without affecting ubiquitin conjugation." *Journal of Biological Chemistry* 259.5 (1984): 2803-2809.

37. Barbul, Adrian. "Proline precursors to sustain mammalian collagen synthesis." The *Journal of nutrition* 138.10 (2008): 2021S-2024S.

38. Chang, Jinhong, et al. "Imino sugar glucosidase inhibitors as broadly active anti-filovirus agents." *Emerging Microbes & Infections* 2.11 (2013): e77.

39. Sanchez, Anthony, et al. "Analysis of human peripheral blood samples from fatal and nonfatal cases of Ebola (Sudan) hemorrhagic fever: cellular responses, virus load, and nitric oxide levels." Journal of virology 78.19 (2004): 10370-10377.

40. Johnson, E., et al. "Lethal experimental infections of rhesus monkeys by aerosolized Ebola virus." International journal of experimental pathology 76.4 (1995): 227.

41. Villinger, Francois, et al. "Markedly elevated levels of interferon (IFN)-γ, IFN-α, interleukin (IL)-2, IL-10, and tumor necrosis factor-α associated with fatal Ebola virus infection." Journal of Infectious Diseases 179. Supplement 1 (1999): 5188-S191.

42. Kaletsky, Rachel L., Graham Simmons, and Paul Bates. "Proteolysis of the Ebola virus glycoproteins enhances virus binding and infectivity." Journal of virology 81.24 (2007): 13378-13384.

43. Schornberg, Kathryn, et al. "Role of endosomal cathepsins in entry mediated by the Ebola virus glycoprotein." Journal of virology 80.8 (2006): 4174-4178.
44. Chandran, Kartik, et al. "Endosomal proteolysis of the Ebola virus glycoprotein is necessary for infection." Science 308.5728 (2005): 1643-1645.
45. World Health Organization. "Ebola response roadmap." (2014).
46. Taylor, Ethan Will, and Chandra Sekar Ramanathan. "Theoretical Evidence that the Ebola Virus Zaire Strain May Be Selenium-Dependent: A Factor in Pathogenesis and Viral Outbreaks?." Journal of Orthomolecular Medicine 10 (1995): 131-138.
47. Jedinak, Andrej, et al. "Antiprotease and antimetastatic activity of ursolic acid isolated from *Salvia officinalis*." ZEITSCHRIFT FUR NATURFORSCHUNG C61.11/12 (2006): 777.
48. Awasthi, Niranjan, and B. J. Wagner. "Upregulation of heat shock protein expression by proteasome inhibition: an antiapoptotic mechanism in the lens." Investigative ophthalmology & visual science 46.6 (2005): 2082-2091.
49. Fauci, Anthony S. "Ebola-underscoring the global disparities in health care resources." *New England Journal of Medicine* (2014).
50. Leffel, Elizabeth K., and Douglas S. Reed. "Marburg and Ebola viruses as aerosol threats." *Biosecurity and bioterrorism: biodefense strategy, practice, and science* 2.3 (2004): 186-191.
51. Jaax, N., et al. "Transmission of Ebola virus (Zaire strain) to uninfected control monkeys in a biocontainment laboratory." *The Lancet* 346.8991 (1995): 1669-1671.
52. Bosio, Catharine M., et al. "Ebola and Marburg viruses replicate in monocyte-derived dendritic cells without inducing the production of cytokines and full maturation." *Journal of Infectious Diseases* 188.11 (2003): 1630-1638.
53. Guo, Shujuan, and Luisa A. DiPietro. "Factors affecting wound healing." *Journal of dental research* 89.3 (2010): 219-229.
54. Baize, S., et al. "Inflammatory responses in Ebola virus-infected patients."*Clinical & Experimental Immunology* 128.1 (2002): 163-168.
55. US20030039702 Inventors Shiro Shigeta, Toshihiro Yamase Poylin, Vitaliy, et al. "The NF-κB Inhibitor Curcumin Blocks Sepsis-Induced Muscle Proteolysis." *Mediators of inflammation* 2008 (2008).
56. Chan, Stephen Y., et al. "Folate receptor-α is a cofactor for cellular entry by Marburg and Ebola viruses." *Cell* 106.1 (2001): 117-126.
57. Alemdaroglu, N. Ceren, et al. "Inhibition of folic acid uptake by catechins and tea extracts in Caco-2 cells." *Planta medica* 73.1 (2007): 27.
58. Lim, Siew Pheng, et al. "Small molecule inhibitors that selectively block dengue virus methyltransferase." Journal of Biological Chemistry 286.8 (2011): 6233-6240.
59. Harrington, Elizabeth O., et al. "Barrier dysfunction and RhoA activation are blunted by homocysteine and adenosine in pulmonary endothelium." American Journal of Physiology-Lung Cellular and Molecular Physiology 287.6 (2004): L1091-L1097.
60. Lu, Qing, et al. "Adenosine protected against pulmonary edema through transporter- and receptor A2-mediated endothelial barrier enhancement." American Journal of Physiology-Lung Cellular and Molecular Physiology 298.6 (2010): L755-L767.
61. Chou, Ting-Chao, and Paul Talalay. "Quantitative analysis of dose-effect relationships: the combined effects of multiple drugs or enzyme inhibitors." Advances in enzyme regulation 22 (1984): 27-55.
62. Khafif, Avi, et al. "Quantitation of chemopreventive synergism between (−)-epigallocatechin-3-gallate and curcumin in normal, premalignant and malignant human oral epithelial cells." Carcinogenesis 19.3 (1998): 419-424.
63. Paul, Atish T., Vikrantsinh M. Gohil, and Kamlesh K. Bhutani. "Modulating TNF-α signaling with natural products." Drug discovery today 11.15 (2006): 725-732.
64. Bray, Mike, John Driscoll, and John W. Huggins. "Treatment of lethal Ebola virus infection in mice with a single dose of an <i> S</i>-adenosyl-1-homocysteine hydrolase inhibitor." Antiviral research 45.2 (2000): 135-147.
65. Borrmann, Steffen, et al. "Fosmidomycin-clindamycin for *Plasmodium falciparum* infections in African children." Journal of Infectious Diseases 189.5 (2004): 901-908.
66. Klaus, Christine R., et al. "DOT1L Inhibitor EPZ-5676 Displays Synergistic Antiproliferative Activity in Combination with Standard of Care Drugs and Hypomethylating Agents in MLL-Rearranged Leukemia Cells." Journal of Pharmacology and Experimental Therapeutics 350.3 (2014): 646-656.
67. Bernt, Kathrin M., and Scott A. Armstrong. "Targeting epigenetic programs in MLL-rearranged leukemias." ASH Education Program Book 2011.1 (2011): 354-360.
68. Wenyu Yu, Emma J. Chory, Amy K. Wernimont, Wolfram Tempel, Alex Scopton, Alexander Federation, Jason J. Marineau, Jun Qi, Dalia Barsyte-Lovejoy, Joanna Yi, Richard Marcellus, Roxana E. Iacob, John R. Engen, Erno Wienholds, Fengling Li, Javier Pineda, Guillermina Estiu, Tatiana Shatseva, Taraneh Hajian, Rima Al-awar, John E. Dick, Masoud Vedadi, Peter J. Brown, Cheryl H. Arrowsmith*, James E. Bradner*, Matthieu Schapira*. Nature Communications 3: 1288doi:10.1038/ncomms2304 (2012)
69. Yu W, et al. Catalytic site remodelling of the DOT1L methyltransferase by selective inhibitors. (2012) Nat Commun. 3:1288.
70. Gehring, Gerrit, et al. "The clinically approved drugs amiodarone, dronedarone and verapamil inhibit filovirus cell entry." Journal of Antimicrobial Chemotherapy (2014): dku091.
71. Shurtleff, Amy C., et al. "HSPA5 is an essential host factor for Ebola virus infection." Antiviral research 109 (2014): 171-174.
72. Habtemariam, Solomon. "Natural inhibitors of tumour necrosis factor-alpha production, secretion and function." Planta medica 66.4 (2000): 303-313.
73. Salom, Hugo Mario Galindo, et al. "Vitamin C Mega Dose vs. Standard Dose in Smokers with Subclinical Hypovitaminosis C, A Controlled Randomised Clinical Trial—a short review."
74. Smith, Lendon H., and F. R. Klenner. "Clinical guide to the use of vitamin C." SEANET Corporation-Internet Services for the Puget Sound Region. http://www.seanet.com/~alexs/ascorbate/198x/smith-lh-clinical_guide_1988. htm (accessed Jul. 16, 2012) (1988).
75. Taylor, Ethan Will, and Chandra Sekar Ramanathan. "Theoretical Evidence that the Ebola Virus Zaire Strain May Be Selenium-Dependent: A Factor in Pathogenesis and Viral Outbreaks?." Journal of Orthomolecular Medicine 10 (1995): 131-138.

76. Leyssen, Pieter, Erik De Clercq, and Johan Neyts. "Perspectives for the Treatment of Infections with Flaviviridae." Clinical microbiology reviews 13.1 (2000): 67-82.

77. Lee-Huang, Sylvia, et al. "Discovery of small-molecule HIV-1 fusion and integrase inhibitors oleuropein and hydroxytyrosol: Part I. Integrase inhibition." Biochemical and biophysical research communications 354.4 (2007): 872-878.

78. Takhampunya, Ratree, et al. "Inhibition of dengue virus replication by mycophenolic acid and ribavirin." Journal of general virology 87.7 (2006): 1947-1952.

79. Diamond, Michael S., Marcus Zachariah, and Eva Harris. "Mycophenolic acid inhibits dengue virus infection by preventing replication of viral RNA." Virology 304.2 (2002): 211-221.

80. Kasmi, Yassine. "Étude in silico des effets inhibitrices des Oleuropein, Kaempferol, et Quercetin sur le Protéine VP30 de Ebola Virus [In silico study of the inhibitory effects of Oleuropein, Kaempferol, and Quercetin on the VP30 protein from Ebola Virus]." (2014).

81. Covre, Alessia, et al. "Immunomodulatory activity of SGI-110: a basis for novel chemo-immunotherapeutic combinations in cancer treatment." Journal for immunotherapy of cancer 1. Suppl 1 (2013): P71.

82. Zagni, C., U. Chiacchio, and A. Rescifina. "Histone methyltransferase inhibitors: novel epigenetic agents for cancer treatment." Current medicinal chemistry 20.2 (2013): 167-185.

83. Kantarjian, Hagop M., et al. "First clinical results of a randomized phase 2 study of SGI-110, a novel subcutaneous (SQ) hypomethylating agent (HMA), in adult patients with acute myeloid leukemia (AML)." Blood 122.21 (2013): 497-497.

84. Liu, Feng, et al. "Optimization of cellular activity of G9a inhibitors 7-aminoalkoxy-quinazolines." Journal of medicinal chemistry 54.17 (2011): 6139-6150.

85. Knutson, Sarah K., et al. "Durable tumor regression in genetically altered malignant rhabdoid tumors by inhibition of methyltransferase EZH2." Proceedings of the National Academy of Sciences 110.19 (2013): 7922-7927.

The invention claimed is:

1. A method for reducing a load of an infectious RNA virus causing a hemorrhagic pathogenic disease in a mammalian subject, the method comprising administering to said subject a DOT1L inhibitor compound, said compound adapted to reduce a load of said RNA virus by at least 50% in said mammalian subject, wherein said compound has a therapeutic index ($TI=LD_{50}:ED_{50}$) greater than 30 in said mammalian subject against said infectious RNA virus, wherein said infectious RNA virus is Ebola virus.

2. A method according to claim 1, wherein said DOT1L inhibitor compound has an IC80 of less than 1 micromolar.

3. A method according to claim 1, wherein said DOT1L inhibitor compound has an ED50 of less than 1 micromolar.

4. A method according to claim 1, wherein said DOT1L inhibitor compound is formulated in a pharmaceutical composition.

5. A method according to claim 4, wherein said DOT1L inhibitor compound is EPZ5676.

6. A method according to claim 4, wherein the pharmaceutical composition is provided in a dosage form selected from an injectable dosage form, infusible dosage form, inhalable dosage form, edible dosage form, slow release dosage form, oral dosage form or combinations thereof.

7. A method according to claim 1, wherein said mammalian subject is human.

8. A method according to claim 1, wherein said load is reduced by 80% or more in said mammalian subject.

9. A method according to claim 1, wherein said administering step is performed by oral, parenteral, transdermal, intra-venous or intra-muscular administration.

* * * * *